United States Patent
Brown et al.

[11] Patent Number: 6,167,362
[45] Date of Patent: *Dec. 26, 2000

[54] MOTIVATIONAL TOOL FOR ADHERENCE TO MEDICAL REGIMEN

[75] Inventors: Stephen J. Brown, Woodside; Alan Miller, Mountain View, both of Calif.

[73] Assignee: Health Hero Network, Inc., Mountain View, Calif.

[*] Notice: This patent is subject to a terminal disclaimer.

[21] Appl. No.: 09/264,760

[22] Filed: Mar. 9, 1999

Related U.S. Application Data

[63] Continuation-in-part of application No. 08/781,278, Jan. 10, 1997, Pat. No. 5,956,501.

[51] Int. Cl.$^7$ .................................................. G06N 3/00
[52] U.S. Cl. .......................... 703/11; 434/238; 434/262; 463/9
[58] Field of Search .................. 703/11, 6; 434/238, 434/262; 463/9

[56] References Cited

U.S. PATENT DOCUMENTS

| | | | |
|---|---|---|---|
| 5,572,646 | 11/1996 | Kawai et al. | 345/501 |
| 5,659,691 | 8/1997 | Durward et al. | 345/329 |
| 5,754,740 | 5/1998 | Fukuoka et al. | 706/58 |
| 5,956,501 | 9/1999 | Brown | 703/11 |
| 5,966,526 | 10/1999 | Yokoi | 703/11 |
| 5,971,855 | 10/1999 | Ng | 463/42 |
| 5,983,003 | 11/1999 | Lection et al. | 709/202 |

OTHER PUBLICATIONS

"Nano Page," 1997 [retrieved on Apr. 23, 2000], Retrieved from <URL:www.virtualpet.com/vp/farm/nano/nano.htm>.
Polson, Gary "Recent Developments and Trends in Keychain Virtual Pets," 1997 [retrieved on Apr. 23, 2000], Retrieved from <URL:www.virtualpet.com/vp/future/trends1a.htm>.
"Furture of the Virtual Pet Industry," 1997 [retrieved on Apr. 23, 2000], Retrieved from <URL:www.virtualpet.com/vp/future/future.htm>.
"Giga Pets," 1997 [retrieved on Apr. 23, 2000], Retrieved from <URL:www.virtualpet.com/vp/farm/gigapet/gigapet.htm>.
"Tamagotchi," 1997 [retrieved on Apr. 23, 2000], Retrieved from <URL:www.virtualpet.com/vp/farm/lleg/lleg.htm>.
"Virtual Pet Product Reviews," 1997 [retrieved on Apr. 23, 2000], Retrieved from <URL:www.virtualpet.com/vp/farm/reviews/reviews,htm>.
Octogotchi Instruction Manual, 1997.
Dino–Kun Instruction Manual, 1997.

(List continued on next page.)

*Primary Examiner*—Kevin J. Teska
*Assistant Examiner*—Kyle J. Choi
*Attorney, Agent, or Firm*—Black Lowe & Graham

[57] ABSTRACT

A method and system for simulating a chronic disease condition comprises a compact, easy to use electronic device. A virtual pet device for providing at least one disease control parameter value and a general health status value for the virtual pet having a chronic medical condition includes: a microprocessor having a memory, a housing, an input unit external to the housing, and a display integral with the housing. The device may include a plurality of icons and a plurality of input buttons for inputting medical regimen-related data into the device. Graphics are provided for portraying a plurality of stages in the development and maturation of the virtual pet, as well as for displaying at least one disease control parameter. An audio unit provides sound synchronized to the graphics, and includes an alarm function related to scheduled medication administration. A total score representing progress towards graduation and general health of the virtual pet may be displayed as a numerical value, together with values for at least one disease control parameter. The device provides an effective motivational and educational tool for patients required to follow a long term medical regimen.

34 Claims, 11 Drawing Sheets

OTHER PUBLICATIONS

"Virtual Tomagutchi,"1998 [retrieved Apr. 23, 2000], Retrieved from <URL:www.sttf.org/english/action/tomagutchi.html>.

DigiPet Instruction Manual, 1997.

"Theme Hospital," product review 1996, [retrieved Apr. 21, 2000], Retrieved from <URL:www.vigilante.co.uk/ep/misc/hospital.htm>.

PHYSIOLOGICAL PARAMETERS ENTRY SCREEN — 41

- BODY MASS (KG): [78] ~43
- METABOLISM RATE: [HIGH]
- FITNESS LEVEL: [LOW]
- INSULIN SENSITIVITIES:
  - HEPATIC (SH) [0.4]
  - PERIPHERAL (SP) [0.6]

[OK] ~45
[CANCEL] ~47

*FIG. 2*

SELF-CARE PARAMETERS ENTRY SCREEN — 52

| FOOD EXCHANGES: | BREAKFAST | LUNCH | DINNER |
|---|---|---|---|
| TIME (HH:MM) | 08:00 | 12:00 | 18:00 ~51 |
| CARBOHYDRATE (G) | 40 | 40 | 30 ~53 |

| INSULIN INJECTIONS: | DOSE 1 | DOSE 2 | DOSE 3 |
|---|---|---|---|
| TIME (HH:MM) | 08:00 | 12:00 | 18:00 |
| DOSE (UNITS) | 15 | 10 | 12 |

| EXERCISE: | SESSION 1 | SESSION 2 | SESSION 3 |
|---|---|---|---|
| TIME (HH:MM) | 15:00 | | |
| DURATION (15 MIN. UNITS) | 2 | | |

55~ [OK]    [CANCEL] ~57

*FIG. 3*

| t | R(t) | X(t) | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 0 | 0 | 0 | 4 | -40 | -5 |
| 10:00 | 160 | 160 | 0 | 0 | 0 | 4 | -40 | -5 |
| 12:00 | 100 | 100 | 0 | 0 | 0 | 4 | -40 | -5 |
| 15:00 | 140 | 140 | 0 | 0 | 0 | 4 | -40 | -5 |
| 18:00 | 100 | 100 | 0 | 0 | 0 | 4 | -40 | -5 |
| 20:00 | 180 | 180 | 0 | 0 | 0 | 4 | -40 | -5 |
| 22:00 | 120 | 120 | 0 | 0 | 0 | 4 | -40 | -5 |

| t | R(t) | X(t) | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 10 | 0 | 0 | 4 | -40 | -5 |
| 10:00 | 160 | 200 | 0 | 0 | 0 | 4 | -40 | -5 |
| 12:00 | 100 | 140 | 0 | 0 | 0 | 4 | -40 | -5 |
| 15:00 | 140 | 180 | 0 | 0 | 4 | 4 | -40 | -5 |
| 18:00 | 100 | 120 | 0 | 0 | 0 | 4 | -40 | -5 |
| 20:00 | 180 | 200 | 0 | 0 | 0 | 4 | -40 | -5 |
| 22:00 | 120 | 140 | 0 | 0 | 0 | 4 | -40 | -5 |

| t | R(t) | X(t) | $S_1(t) - O_1(t)$ | $S_2(t) - O_2(t)$ | $S_3(t) - O_3(t)$ | $K_1$ | $K_2$ | $K_3$ |
|---|---|---|---|---|---|---|---|---|
| 8:00 | 80 | 80 | 10 | 0 | 0 | 4 | -40 | -5 |
| 10:00 | 160 | 200 | 0 | 1 | 0 | 4 | -40 | -5 |
| 12:00 | 100 | 100 | 0 | 0 | 0 | 4 | -40 | -5 |
| 15:00 | 140 | 140 | 0 | 0 | 4 | 4 | -40 | -5 |
| 18:00 | 100 | 80 | 5 | 0 | 0 | 4 | -40 | -5 |
| 20:00 | 180 | 180 | 0 | 0 | 0 | 4 | -40 | -5 |
| 22:00 | 120 | 120 | 0 | 0 | 0 | 4 | -40 | -5 |

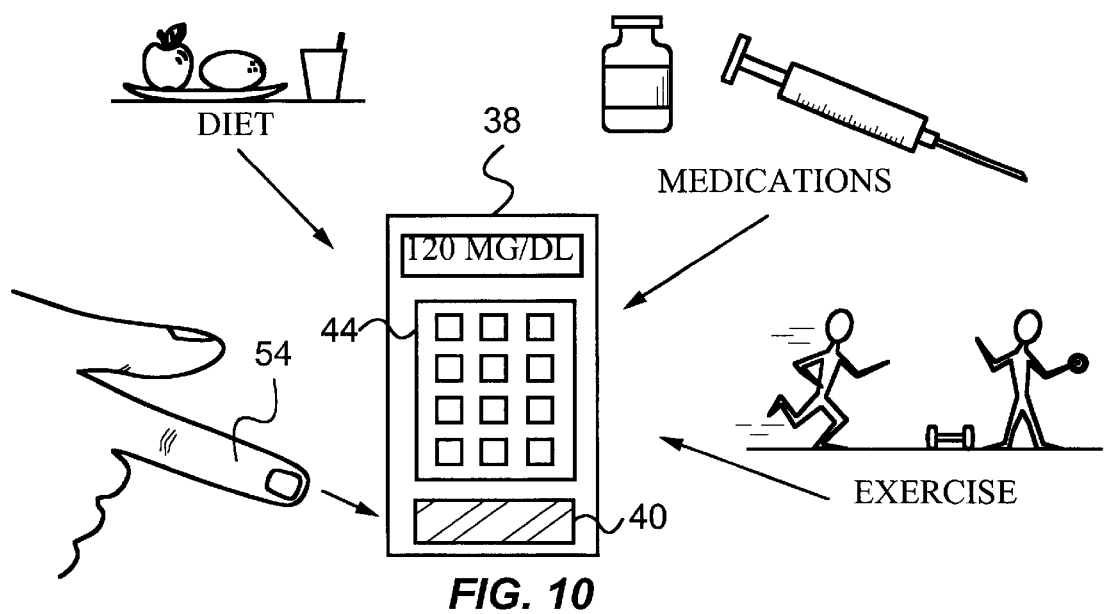
FIG. 10
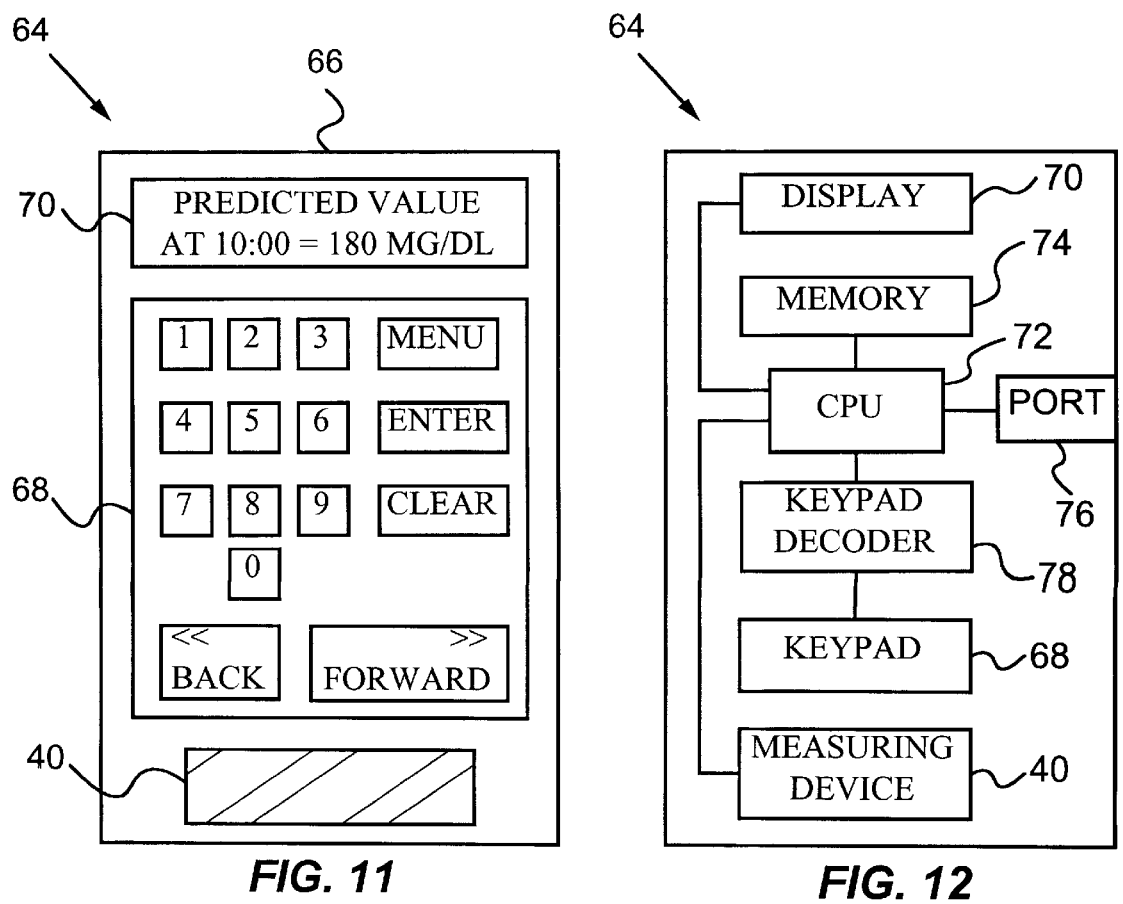
FIG. 11   FIG. 12

MOTIVATIONAL TOOL FOR ADHERENCE TO MEDICAL REGIMEN

RELATED U.S. APPLICATION DATA

This application is a continuation-in-part of application Ser. No. 08/781,278, filed Jan. 10, 1997, now U.S. Pat. No. 5,956,501 and related to application Ser. No. 08/898,711, filed Jul. 22, 1997, now abandoned which are incorporated by reference herein.

BACKGROUND OF THE INVENTION

1. Field of the Invention

The present invention relates generally to disease management systems and methods. The present invention also relates generally to disease simulation systems and methods, and in particular to a device and methods for simulating a disease control parameter and for predicting the effect of patient self-care actions on the disease control parameter.

This invention further relates to a device for advising a patient of the consequences of life-style and adherence to a medical regimen on disease control parameters. The present invention further relates to an electronic or virtual pet device. More particularly, the invention relates to a virtual pet device which simulates patient disease control parameters in response to a virtual medical regimen imposed for the treatment of a chronic disease or disorder.

2. Background of the Related Art

Managing a chronic disease or ongoing health condition requires the monitoring and controlling of a physical or mental parameter of the disease Exams of these disease control parameters include blood glu diabetes, respiratory flow in asthma, blood pressure in hypertension, cholesterol in cardiovascular disease, weight in eating disorders, T-cell or viral count in HIV, lung function or body weight in cystic fibrosis, and frequency or timing of episodes in mental health disorders. Because of the continuous nature of these diseases, their corresponding control parameters must be monitored and controlled on a regular basis by the patients themselves outside of a medical clinic.

Typically, the patients monitor and control these parameters in clinician assisted self-care or outpatient treatment programs. In these treatment programs, patients are responsible for performing self-care actions which impact the control parameter. Patients are also responsible for measuring the control parameter to determine the success of the self-care actions and the need for further adjustments. The successful implementation of such a treatment program requires a high degree of motivation, training, and understanding on the part of the patients to select and perform the appropriate self-care actions.

One method of training patients involves demonstrating the effect of various self-care actions on the disease control parameter through computerized simulations. Several computer simulation programs have been developed specifically for diabetes patients. Examples of such simulation programs include BG Pilot™ commercially available from Raya Systems, Inc. of 2570 El Camino Real, Suite 520, Mountain View, Calif. 94040 and AIDA freely available on the World Wide Web at the Diabetes UK web site.

Both BG Pilot™ and AIDA use mathematical compartmental models of metabolism to attempt to mimic various processes of a patient's physiology. For example, insulin absorption through a patient's fatty tissue into the patient's blood is represented as a flow through several compartments with each compartment having a different flow constant. Food absorption from mouth to stomach and gut is modeled in a similar manner. Each mathematical compartmental model uses partial differential equations and calculus to simulate a physiological process.

This compartmental modeling approach to disease simulation has several disadvantages. First, understanding the compartmental models requires advanced mathematical knowledge of partial differential equations and calculus which is far beyond the comprehension level of a typical patient. Consequently, each model is an unfathomable "black box" to the patient who must nevertheless trust the model and rely upon it to learn critical health issues.

A second disadvantage of the compartmental modeling approach is that a new model is needed for each new disease to be simulated. Many diseases involve physiological processes for which accurate models have not been developed. Consequently, the mathematical modeling approach used in BG Pilot™ and AIDA is not sufficiently general to extend simulations to diseases other than diabetes.

A further disadvantage of the modeling approach used in BG Pilot™ and AIDA is that the mathematical models are not easily customized to an individual patient. As a result, BG Pilot™ and AIDA are limited to simulating the effect of changes in insulin and diet on the blood glucose profile of a typical patient. Neither of these simulation programs may be customized to predict the effect of changes in insulin and diet on the blood glucose profile of an individual patient.

Cystic Fibrosis

Cystic fibrosis (CF) is a hereditary disease or genetic disorder caused by a single gene. About 1 in 20 persons carries a gene for the disorder. A key feature of cystic fibrosis is the production in the bronchial tubes of viscous mucus which is difficult to expectorate and which therefore tends to accumulate in the bronchial tubes. The mucus provides a breeding ground for microorganisms, which may lead to respiratory infections, including pneumonia. Untreated, a child with cystic fibrosis is likely to experience recurrent respiratory infections. Repeated bouts of pneumonia in children with cystic fibrosis usually lead to bronchiecstasis, a condition which makes the lungs even more susceptible to further bouts of pneumonia.

Treatment with various medications, including antibiotics, is enabling more cystic fibrosis patients to survive into early adulthood. In addition, in order to keep the lungs as free of mucus as possible, respiratory physical therapy, including postural drainage, may be called for.

Recently, treatment with Pulmozyme™ has been introduced as a means of reducing the severity of one of the major symptoms of the disorder, i.e. the accumulation of thick mucus. Pulmozyme™ contains an enzyme which breaks down DNA in the mucus, thereby decreasing the viscosity of the mucus and facilitating expectoration of the mucus.

Another feature of cystic fibrosis is a deficiency in digestive enzyme production from the pancreas. Consequently, in an untreated child, ingested food retains its fat components and is only minimally digested, leading to malabsorption. As a result the child gains little weight, and at the same time the stools are large, pale, and greasy. This condition may be treated by taking pancreatic enzymes. At the same time it is advisable to decrease the amount of fat in the child's diet.

In summary, cystic fibrosis is a debilitating condition which affects many children in the U.S. and elsewhere. Due to the chronic nature of the condition and its symptoms, cystic fibrosis represents a major burden to the child and the child's family.

In order to increase a child's chances of survival to adulthood, strict adherence to a complex, multicomponent medical regimen is indicated. A medical regimen for a child afflicted with cystic fibrosis typically includes daily administration of medications, including Pulmozyme™ and oral antibiotics, as well as pancreatic enzymes, vitamin supplements, and chest physical therapy. Such a medical regimen is described more fully hereinbelow with reference to the virtual pet device of the present invention.

Due to the on-going, long-term nature of the cystic fibrosis disorder and the medical treatment indicated for it, a child (and possibly the child's family) may tend to lose interest in the medical regimen. This is especially true when little or no long-term improvement in the patient's condition is attained. This situation can lead to discouragement and a lack of interest in medical treatment. Any device or method which can serve to educate or involve the child in his/her medical treatment, or which can directly motivate the child to greater adherence to the indicated medical regimen is of great benefit. This is so because failure to adhere to a recommended medical regimen usually signals a death knell for the cystic fibrosis patient.

Electronic, hand-held, interactive virtual pets are extremely popular with children, especially with those in the 5–12 years old range. Some current examples of these devices are Giga-pet (manufactured by Tiger Electronics, Ltd., Vernon Hills, Ill.), Nano Pet (Playmates Toys, Inc., Costa Mesa, Calif.), and Tamagotchi (Bandai America, Inc., Cypress, Calif.) etc. In many cases, a child's virtual pet is his/her more or less constant companion. For example, the pet may be the first object picked up by the child upon waking in the morning, may accompany the child to school during the day, and be the last item to be interacted with by the child at bedtime. Due to the high level of compatibility between a child and this type of device, and the amount of time spent "together", an appropriately designed pet has the potential for a substantial impact on the child's routine, state of mind, and well-being. For example, a virtual pet with a certain set of characteristics or needs can convey those characteristics or needs to a child in a way that formal training or interaction with less "compatible" devices would fail to achieve.

The present invention relates to an electronic virtual pet device, wherein the virtual pet is afflicted with a chronic disease or disorder. An appropriate or standardized medical regimen for the pet may be programmed into a microprocessor of the device, together with appropriate disease control parameters (e.g. lung function, body weight) for the pet. The child (pet owner) is responsible for entering into the pet information concerning the virtual treatment administered to/received by the pet. Based on such data, the virtual pet device can calculate disease parameter values to be displayed to the child or other owner of the device. If the pet receives appropriate and timely medical treatment according to a recommended or ideal virtual medical regimen, the pet's health will allow him to lead a productive life and to survive into adulthood. On the other hand, if the virtual medical regimen of the pet is inappropriate, the health of the virtual pet will suffer accordingly, and it may die prematurely.

It is worth noting that studies on the involvement of children with their own health care have shown increased compliance to their treatment regimen, increased patient satisfaction with treatment, increased feeling of control, increased sense of competence and independence, and most importantly, improved health, reduced clinical utilization, and reduced health care costs.

SUMMARY

One advantage of the invention is that it provides a device in which the consequences of virtual care provided to a virtual pet can be seen by an operator of the device in a matter of minutes or hours.

Another advantage of the invention is that it provides a disease simulation system which can be used and understood by a young child.

Another advantage of the invention is that it provides a disease simulation system which is sufficiently accurate to teach a patient appropriate self-care actions and sufficiently simple to be understood by the average patient. The invention further provides a disease simulation system which may be used to simulate many different types of diseases, and which may be easily customized to an individual patient.

According to one embodiment, the invention provides a system and method for simulating a disease control parameter and for predicting an effect of patient self-care actions on the disease control parameter. According to the method, a future disease control parameter value $X(t_j)$ at time $t_j$ is determined from a prior disease control parameter value $X(t_i)$ at time $t_i$ based on an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$. In the preferred embodiment, the differentials are multiplied by corresponding scaling factors $K_M$ and the future disease control parameter value $X(t_j)$ is calculated according to the equation:

$$X(t_j) = R(t_j) + (X(t_i) - R(t_i)) + \sum_M K_M (S_M(t_i) - O_M(t_i)) \qquad (1)$$

A preferred system for implementing the method includes an input device for entering the patient self-care values $S_M(t_i)$. The system also includes a memory for storing the optimal control parameter values $R(t_i)$ and $R(t_j)$, the prior disease control parameter value $X(t_i)$, the optimal self-care values $O_M(t_i)$, and the scaling factors $K_M$. A processor in communication with the input device and memory calculates the future disease control parameter value $X(t_j)$. A display is connected to the processor to display the future disease control parameter value $X(t_j)$ to a patient.

In a preferred embodiment, the system further includes a recording device in communication with the processor for recording an actual control parameter value $A(t_i)$ at time $t_i$, an actual control parameter value $A(t_j)$ at time $t_j$, and actual self-care parameters having actual self-care values $C_M(t_i)$ at time $t_i$. The processor adjusts the scaling factors $K_M$ based on the difference between the actual control parameter value $A(t_j)$ and the optimal control parameter value $R(t_j)$, the difference between the actual control parameter value $A(t_i)$ and the optimal control parameter value $R(t_i)$, and the difference between the actual self-care values $C_M(t_i)$ and the optimal self-care values $O_M(t_i)$. Thus, the scaling factors $K_M$ are customized to an individual patient to predict the effect on the disease control parameter of self-care actions performed by the individual patient.

According to another embodiment of the invention, there is provided an electronic device for displaying at least one disease control parameter of a virtual pet, wherein the device includes: a microprocessor having a memory; a housing for housing the microprocessor; a display unit integral with the housing; an input unit for inputting data to the device, wherein the virtual pet comprises a virtual patient having a chronic ailment and requiring adherence to a defined medical regimen.

The above and other advantages are further accomplished by the provision of an electronic device for displaying at least one disease control parameter of a virtual patient, wherein the electronic device includes input means for entering patient self-care values $S_M(t_i)$; a memory for storing optimal control parameter values $R(t_i)$ and $R(t_j)$, a prior disease control parameter value $X(t_i)$, optimal self-care values $O_M(t_i)$, and scaling factors $K_M$; a microprocessor in communication with the input means and the memory for calculating a future disease control parameter value $X(t_j)$ according to the equation:

$$X(t_j) = R(t_j) + (X(t_i) - R(t_i)) + \sum_M K_M(S_M(t_i) - O_M(t_i));$$

and a display connected to the microprocessor for displaying the future disease control parameter value $X(t_j)$.

The above and other advantages are further accomplished by the provision of a method for motivating a patient to adhere to a medical regimen for a chronic medical condition afflicting the patient, including the steps of: providing an electronic device to the patient, wherein the device includes an input unit for entering patient self-care values of patient self-care parameters; a microprocessor having a memory, the microprocessor in communication with the input unit and the memory; and a display unit, wherein the display displays a virtual pet, and wherein the virtual pet has a chronic medical condition mirroring the chronic medical condition afflicting the patient; having the patient enter patient self-care values of patient self-care parameters into the device via the input unit; and obtaining a readout from the device concerning at least one disease control parameter related to the chronic medical condition.

These and other advantages will become more apparent after consideration of the ensuing description and the accompanying drawings.

BRIEF DESCRIPTION OF THE DRAWINGS

FIG. 2 is a sample physiological parameter entry screen according to the invention.

FIG. 3 is a sample self-care parameter entry screen according to the invention.

FIG. 10 is a schematic illustration of the entry of actual parameter values in a recording device of the system of FIG. 1.

FIG. 11 is a schematic diagram of another simulation system according to the invention.

FIG. 12 is a schematic block diagram illustrating the components of the system of FIG. 11.

DETAILED DESCRIPTION

The present invention provides a system and method for simulating a disease control parameter and for predicting an effect of patient self-care actions on the disease control parameter. In the following detailed description, numerous specific details are set forth in order to provide a thorough understanding of the present invention. However, it will be apparent to one of ordinary skill in the art that these specific details need not be used to practice the invention. In other instances, well known structures, interfaces, and processes are not shown in detail to avoid unnecessarily obscuring the present invention.

FIGS. 1–10 illustrate a preferred embodiment of a simulation system according to the invention. The following table illustrates a representative sampling of the types of diseases, patient self-care parameters, and disease control parameters which may be simulated using the system and method of the invention.

| Disease | Patient Self-Care Parameters | Disease Control Parameter |
| --- | --- | --- |
| Diabetes | Insulin, diet, exercise | blood glucose level |
| Asthma | Allergens, exercise, inhaled bronchial dilators, anti-inflammatory medications | peak flow rate |
| Obesity | diet, exercise, metabolism altering medications | Weight |
| Hypertension | diet, exercise, stress reduction, blood pressure medications | blood pressure |
| Coronary Artery Disease | diet, exercise, stress reduction, lipid lowering medications | Cholesterol |
| Panic Disorder | stress reduction, anti-depressant medications | number of episodes |
| Nicotine Addiction | cigarettes smoked, coping behaviors | urges to smoke |

The above table is not intended as an exhaustive list, but merely as a representative sampling of the types of diseases and disease control parameters which may be simulated. A preferred embodiment will first be described with reference to a single disease, diabetes, having a single disease control parameter, a blood glucose level. However, it is to be understood that the system and method of the invention are sufficiently flexible to simulate any disease which has a measurable control parameter and which requires patient self-care actions.

Figure 1:
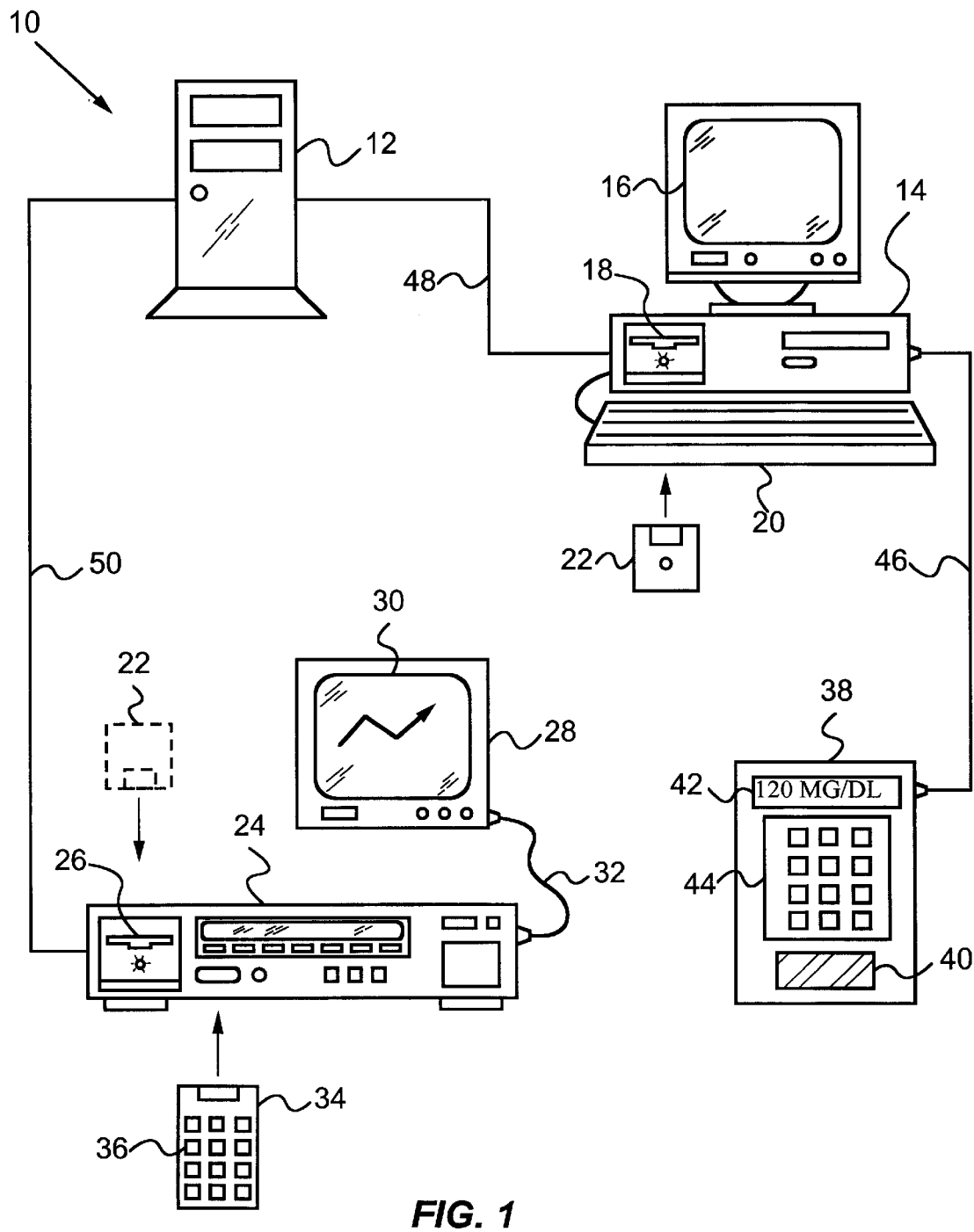
FIG. 1 is a schematic diagram of a simulation system according to the invention.

Referring to FIG. 1, a simulation system generally indicated at 10 includes a server 12 having a processor and memory for executing a simulation program which will be described in detail below. Server 12 is in communication with a healthcare provider computer 14 through a network link 48. Healthcare provider computer 14 is preferably a personal computer located at a healthcare provider site, such as a doctor's office.

Server 12 is also in communication with a patient multi-media processor 24 through a network link 50. Patient multi-media processor 24 is located at a patient site, typically the patient's home. In the preferred embodiment, server 12 is a world wide web server, multi-media processor 24 is a web TV processor for accessing the simulation program on server 12, and links 48 and 50 are Internet links. Specific techniques for establishing client/server computer systems in this manner are well known in the art.

Healthcare provider computer 14 includes a processor and memory, a standard display 16, and a keyboard 20. Computer 14 further includes a card slot 18 for receiving a data storage card, such as a smart card 22. Computer 14 is designed to read data from card 22 and write data to card 22. Patient multi-media processor 24 includes a corresponding card slot 26 for receiving card 22. Processor 24 is designed to read data from card 22 and write data to card 22. Thus, healthcare provider computer 14 communicates with patient multi-media processor 24 via smart card 22. Such smart card data communication systems are also well known in the art.

Multi-media processor 24 is connected to a display unit 28, such as a television, by a standard connection cord 32. Display unit 28 has a screen 30 for displaying simulations to the patient. An input device 34, preferably a conventional hand-held remote control unit or keyboard, is in signal communication with processor 24. Device 34 has buttons or keys 36 for entering data in processor 24.

System 10 also includes an electronic recording device 38 for recording actual control parameter values and patient self-care data indicating actual self-care actions performed by the patient. Recording device 38 includes a measuring device 40 for producing measurements of the disease control parameter, a keypad 44 for entering the self-care data, and a display 42 for displaying the control parameter values and self-care data to the patient.

Recording device 38 is preferably portable so that the patient may carry device 38 and enter the self-care data at regular monitoring intervals. Device 38 is preferably connectable to healthcare provider computer 14, e.g., via a standard connection cord 46, so that the control parameter values and patient self-care data may be uploaded from device 38 to computer 14. Such recording devices for producing measurements of a disease control parameter and for recording self-care data are well known in the art. For example, U.S. Pat. No. 5,019,974 issued to Beckers on May 28, 1991 discloses such a recording device.

By way of example only, the disease control parameter is the patient's blood glucose level and recording device 38 is a blood glucose meter, as shown in FIG. 10. In this embodiment, measuring device 40 is a blood glucose test strip designed to test blood received from a patient's finger 54. Device 38 may also be capable of recording values of the patient's diet, medications, and exercise durations, which may be entered by the patient through keypad 44. Of course, in alternative embodiments, the recording device may be a peak flow meter for recording a peak flow rate, a cholesterol meter for recording a cholesterol level, etc.

Simulation system 10 of the present invention includes a simulation program which uses a mathematical model to calculate disease control parameter values. The following variables used in the mathematical model are defined as follows:

N=Normal time interval in which patient self-care actions are employed to make a measurable difference in the disease control parameter or a natural rhythm occurs in the disease control parameter. For diabetes and asthma, time interval N is preferably twenty-four hours. For obesity or coronary artery disease, time interval N is typically three to seven days.

$t_1, t_2, \ldots t_i, t_j \ldots t_N$=Time points at which the disease control parameter is measured by a patient. For a daily rhythm control parameter such as a blood glucose level, the time points are preferably before and after meals. For weight or cholesterol control parameters, the time points are preferably once a day or once every second day.

X(t)=Simulated disease control parameter value at time t determined by the simulation program.

R(t)=Optimal control parameter value at time t expected as a normal rhythm value of the disease control parameter at time t if the patient performs optimal self-care actions in perfect compliance from time $t_1$ to the time point immediately preceding time t.

A(t)=actual control parameter value at time t measured by the patient.

$O_M(t_i)$=Optimal self-care parameter values $O_1(t_i)$, $O_2(t_i)$, . . . $O_m(t_i)$ at time $t_i$ expected to produce optimal control parameter value $R(t_j)$ at time $t_j$. For example, a diabetes patient's optimal self-care parameter values include a prescribed dose of insulin, a prescribed intake of carbohydrates, and a prescribed exercise duration.

$S_M(t_i)$=Patient self-care parameter values $S_1(t_i)$, $S_2(t_i)$, . . . $S_m(t_i)$ at time $t_i$ entered in the simulation system by the patient to simulate self-care actions.

$C_M(t_i)$=Actual self-care parameter values $C_1(t_i)$, $C_2(t_i)$, . . . $C_m(t_i)$ at time $t_i$ indicating actual self-care actions performed by the patient at time $t_i$.

$K_M$=Corresponding scaling factors $K_1(t_i)$, $K_2(t_i)$, . . . $K_m$ for weighting the impact on a future disease control parameter value $X(t_j)$ at time $t_j$ which results from differentials between patient self-care values $S_M(t_i)$ and corresponding optimal self-care values $O_M(t_i)$.

With these definitions, future disease control parameter value $X(t_j)$ is calculated according to the equation:

$$X(t_j) = R(t_j) + (X(t_i) - R(t_i)) + \sum_M K_M(S_M(t_i) - O_M(t_i)) \quad (1)$$

Future disease control parameter value $X(t_j)$ at time $t_j$ is determined from a prior disease control parameter value $X(t_i)$ at time $t_i$ based on an optimal control parameter value $R(t_j)$ at time $t_j$, the difference between prior disease control parameter value $X(t_i)$ and an optimal control parameter value $R(t_i)$ at time $t_i$, and a set of differentials between patient self-care values $S_M(t_i)$ and optimal self-care values $O_M(t_i)$. The differentials are multiplied by corresponding scaling factors $K_M$.

Thus, as patient self-care parameter values $S_M(t_i)$ deviate from optimal self-care parameter values $O_M(t_i)$, future disease control parameter value $X(t_j)$ deviates from optimal control parameter value $R(t_j)$ by an amount proportional to scaling factors $K_M$. This mathematical model follows the patient's own intuition and understanding that if the patient performs optimal self-care actions in perfect compliance, the patient will achieve the optimal control parameter value at the next measurement time. However, if the patient deviates from the optimal self-care actions, the disease control parameter value will deviate from the optimal value at the next measurement time.

The simulation program is also designed to generate an entry screen for entry of the patient self-care parameter values. FIG. 3 shows a sample patient self-care parameters entry screen 52 as it appears on display unit 28. The patient self-care parameters include a food exchange parameter expressed in grams of carbohydrates consumed, an insulin dose parameter expressed in units of insulin injected, and an exercise duration parameter expressed in fifteen minute units of exercise performed.

These self-care parameters are illustrative of the preferred embodiment and are not intended to limit the scope of the invention. It is to be understood that many different self-care parameters may be used in alternative embodiments. Screen 52 contains data fields 53 for entering a food exchange parameter value $S_1(t)$, an insulin dose parameter value $S_2(t)$, and an exercise duration parameter value $S_3(t)$. Each data field 53 has a corresponding time field 51 for entering a time point corresponding to the patient self-care parameter value. Screen 52 also includes an OK button 55 and a cancel button 57 for confirming and canceling, respectively, the values entered in screen 52.

Figures 4, 5:
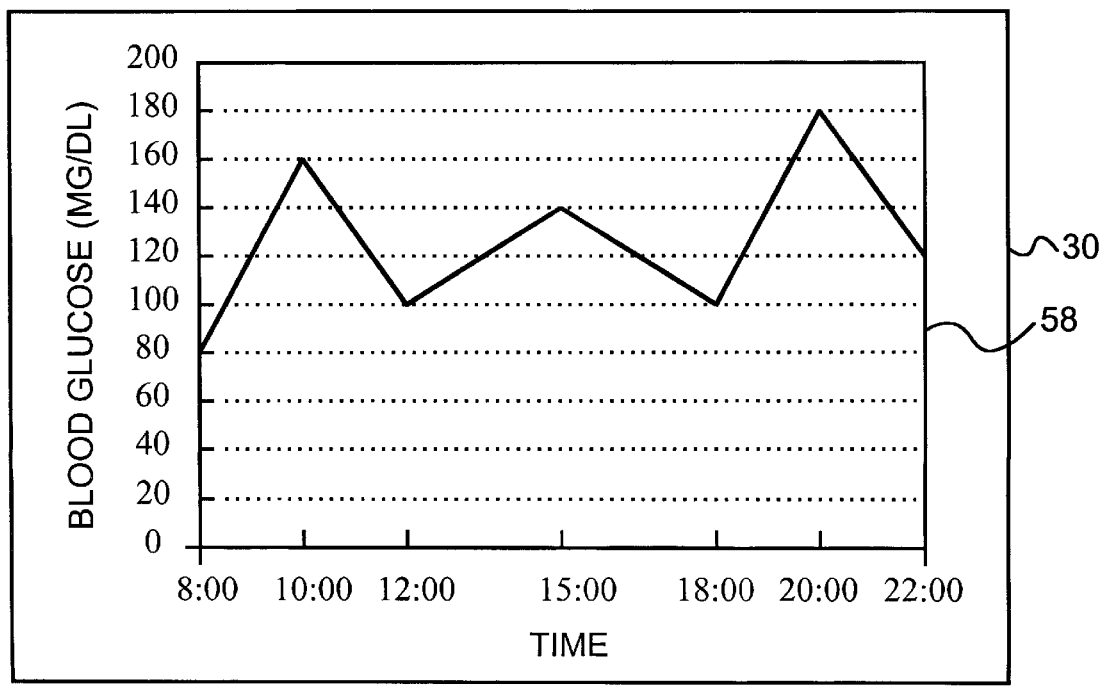
FIG. 4 is a table of values according to the invention.
FIG. 5 is a sample graph of disease control parameter values created from the table of FIG. 4.

FIG. 4 shows a sample table 56 of values created by the simulation program using the data entered by the patient through self-care parameters entry screen 52. Table 56 includes a column of simulated disease control parameter values calculated by the simulation program, as will be explained in the operation section below. The simulation program is further designed to generate graphs of simulated disease control parameter values. FIG. 5 illustrates a sample graph 58 generated from table 56 as it appears on screen 30 of the display unit. Specific techniques for writing a simulation program to produce such a graph are well known in the art.

In a preferred embodiment, healthcare provider computer 14 is programmed to determine scaling factors $K_M$ from values of physiological parameters of the patient. FIG. 2 shows a sample physiological parameter entry screen 41 as it appears on the healthcare provider computer. The physiological parameters of the patient include a body mass, a metabolism rate, a fitness level, and hepatic and peripheral insulin sensitivities. These physiological parameters are illustrative of the preferred embodiment and are not intended to limit the scope of the invention. It is obvious that many different physiological parameters may be used in alternative embodiments. Screen 41 includes data fields 43 for entering physiological parameter values, an OK button 45 for confirming the values, and a cancel button 47 for canceling the values.

Healthcare provider computer 14 stores indexes for determining the scaling factors from the physiological parameters entered. For example, FIG. 4 shows an insulin sensitivity scaling factor $K_2$ corresponding to insulin dose parameter value $S_2(t)$. Computer 14 is programmed to determine from a stored insulin index a value of scaling factor $K_2$ based on the entered values of the patient's body mass and insulin sensitivities. In this example, computer 14 determines a value of −40 for scaling factor $K_2$, indicating that for this patient, one unit of insulin is expected to lower the patient's blood glucose level by 40 mg/dL. Computer 14 is programmed to determine the remaining scaling factors in a similar manner. The specific indexes required to determine the scaling factors from values of a patient's physiological parameters are well known in the art.

In a preferred embodiment, healthcare provider computer 14 is also programmed to adjust scaling factors $K_M$ based on the difference between an actual control parameter value $A(t_j)$ measured at time $t_j$ and optimal control parameter value $R(t_j)$, the difference between an actual control parameter value $A(t_i)$ measured at time $t_i$ and optimal control parameter value $R(t_i)$, and the difference between actual self-care values $C_M(t_i)$ performed by the patient at time $t_i$ and optimal self-care values $O_M(t_i)$.

Scaling factors $K_M$ are adjusted to fit the mathematical model presented above, preferably using a least squares, chi-squares, or similar regressive fitting technique. Specific techniques for adjusting coefficients in a mathematical model are well known in the art. For example, a discussion of these techniques is found in "Numerical Recipes in C: The Art of Scientific Computing", Cambridge University Press, 1988.

Figure 13:
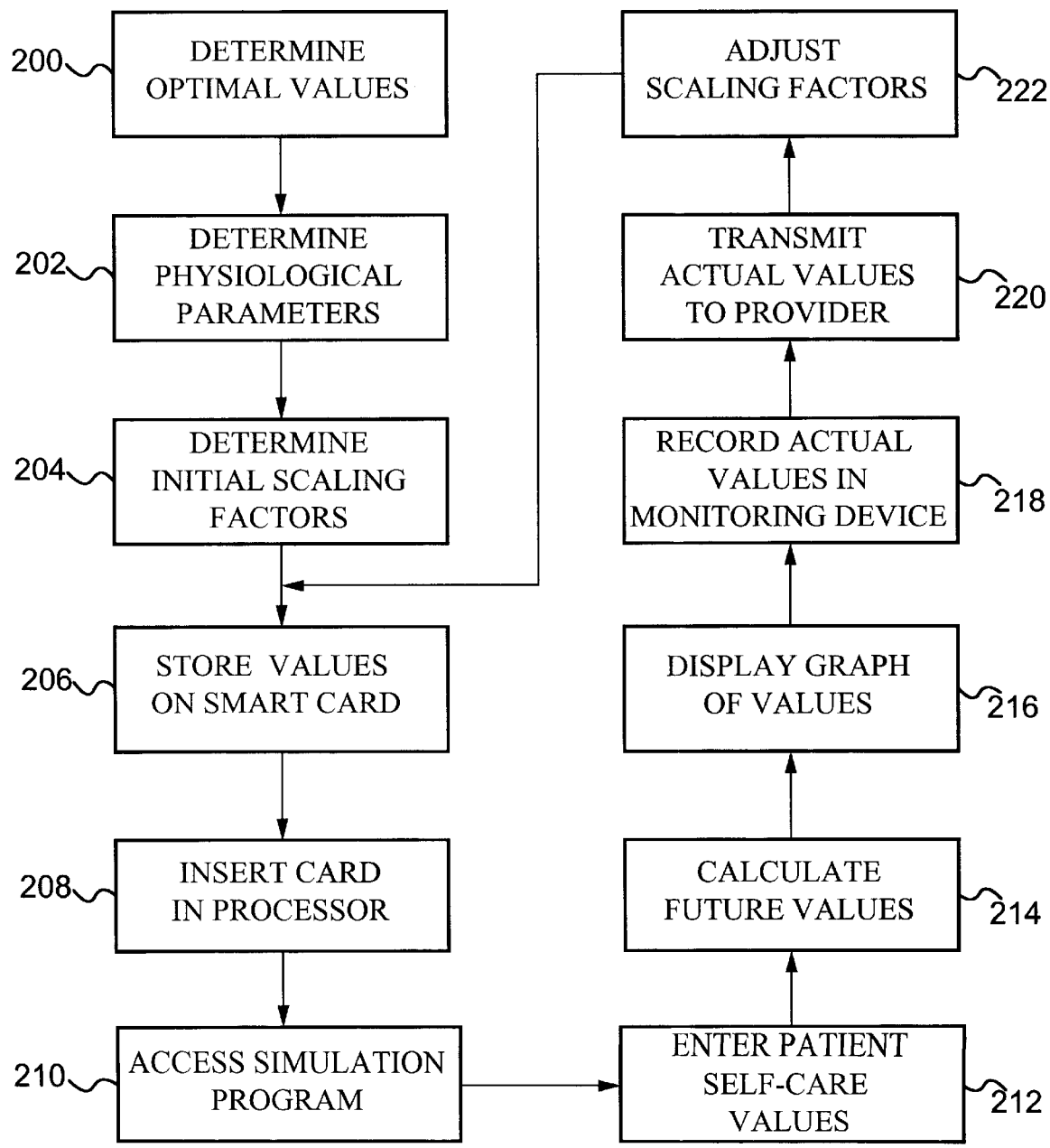
FIG. 13 is a flow chart illustrating steps included in a method of the invention.

The operation of a preferred embodiment is illustrated in FIG. 13. FIG. 13 is a flow chart illustrating a preferred method of using system 10 to simulate the disease control parameter. In step 200, optimal self-care values and optimal control parameter values for each time point are determined for the patient, preferably by the patient's healthcare provider. The optimal self-care values and optimal control parameter values are then entered and stored in provider computer 14.

In a preferred embodiment, the optimal self-care values include an optimal food exchange parameter value $O_1(t)$ expressed in grams of carbohydrates, an optimal insulin dose parameter value $O_2(t)$ expressed in units of insulin, and an optimal exercise duration parameter value $O_3(t)$ expressed in fifteen minute units of exercise. Specific techniques for prescribing optimal self-care values and optimal control parameter values for a patient are well known in the medical field.

In step 202, the healthcare provider determines the physiological parameter values of the patient and enters the physiological parameter values in computer 14 through entry screen 41. As shown in FIG. 2, the physiological parameter values include a body mass, a metabolism rate, a fitness level, and hepatic and peripheral insulin sensitivities. Specific techniques for testing a patient to determine these physiological parameter values are also well known in the medical field.

Following entry of the physiological parameter values, computer 14 determines scaling factors $K_M$ from the stored indexes, step 204. For example, FIG. 4 shows a food exchange scaling factor $K_1$ corresponding to food exchange parameter value $S_1(t)$, an insulin sensitivity scaling factor $K_2$ corresponding to insulin dose parameter value $S_2(t)$, and an exercise duration scaling factor $K_3$ corresponding to exercise duration parameter value $S_3(t)$.

In this example, computer 14 determines a value of 4 for scaling factor $K_1$, a value of −40 for scaling factor $K_2$, and a value of −5 for scaling factor $K_3$. These values indicate that one gram of carbohydrate is expected to raise the patient's blood glucose level by 4 mg/dL, one unit of insulin is expected to lower the patient's blood glucose level by 40 mg/dL, and fifteen minutes of exercise is expected to lower the patient's blood glucose level by 5 mg/dL. Of course, these values are just examples of possible scaling factors for one particular patient. The values of the scaling factors vary between patients in dependence upon the physiological parameter values determined for the patient.

The determined optimal self-care values, optimal control parameter values, and scaling factors are then stored on smart card 22, step 206. Typically, the values are stored on smart card 22 during a patient visit to the healthcare provider. The patient then takes home smart card 22 and inserts smart card 22 in patient multi-media processor 24, step 208. Next, the patient accesses the simulation program on server 12 through multi-media processor 24, step 210.

The simulation program generates self-care parameters entry screen 52, which is displayed to the patient on screen 30 of display unit 28. In step 212, the patient enters patient self-care values $S_M(t)$ and corresponding time points in data fields 53 and 51, respectively, using input device 34. The optimal self-care values, optimal control parameter values, scaling factors, and patient self-care values are transmitted from multi-media processor 24 to server 12 through link 50. In step 214, the simulation program calculates simulated disease control parameter values at each time point according to the equation:

$$X(t_j) = R(t_j) + (X(t_i) - R(t_i)) + \sum_M K_M(S_M(t_i) - O_M(t_i)) \quad (1)$$

Thus, each future disease control parameter value $X(t_j)$ is calculated from optimal control parameter value $R(t_j)$, the difference between prior disease control parameter value $X(t_i)$ and optimal control parameter value $R(t_i)$, and the set of differentials between patient self-care values $S_M(t_i)$ and optimal self-care values $O_M(t_i)$. The differentials are multiplied by corresponding scaling factors $K_M$. In the preferred embodiment, first simulated disease control parameter value $X(t_1)$ at time $t_i$ is set equal to first optimal control parameter value $R(t_1)$ at time $t_1$. In an alternative embodiment, first simulated disease control parameter value $X(t_1)$ is determined from the last disease control parameter value calculated in a prior simulation.

FIGS. 4–5 illustrate a first example of simulated disease control parameter values calculated by the simulation program. Referring to FIG. 4, the simulation program creates table 56 having a time column, an optimal control parameter value column, a simulated control parameter value column, three self-care value differential columns indicating differentials between patient self-care parameter values and optimal self-care parameter values, and three corresponding scaling factor columns for weighting the corresponding self-care value differentials.

Table 56 illustrates the simplest simulation, in which the patient follows the optimal self-care actions in perfect compliance at each time point. In this simulation, each patient self-care parameter value equals its corresponding optimal self-care parameter value, so that the simulated disease control parameter value at each time point is simply equal to the optimal control parameter value at each time point. Referring to FIG. 5, the simulation program generates graph 58 of the simulated disease control parameter values. Graph 58 is presented or displayed to the patient on screen 30 of display unit 28, step 216.

Figures 6, 7:
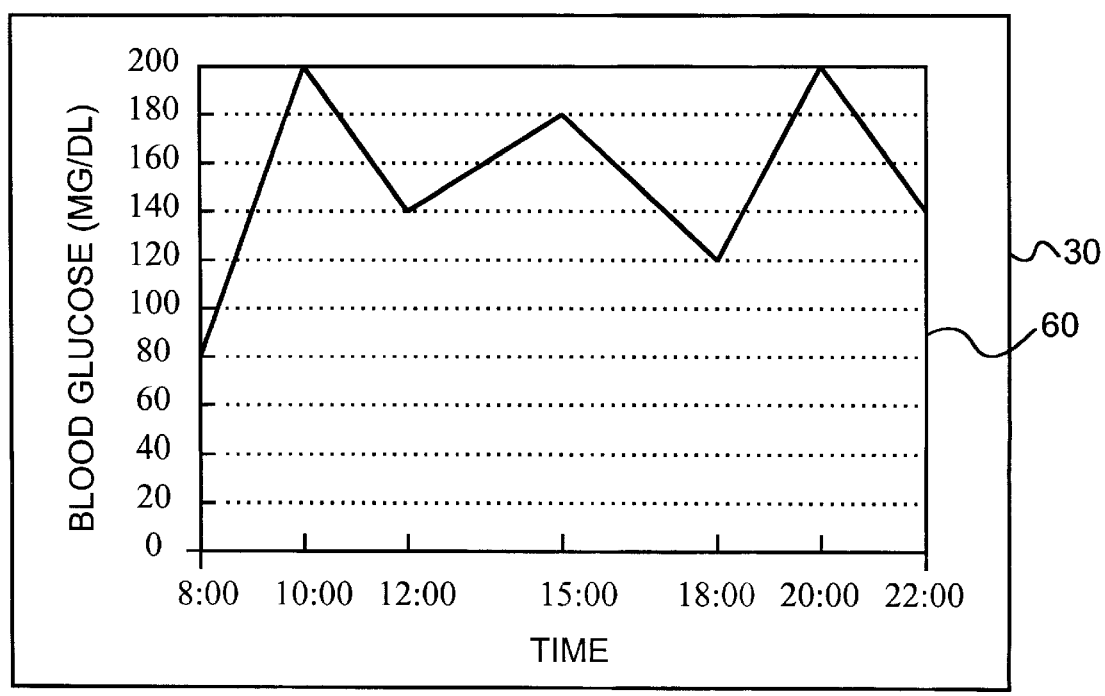
FIG. 6 is another table of values according to the invention.
FIG. 7 is a sample graph of disease control parameter values created from the table of FIG. 6.

FIGS. 6–7 illustrate a second example of simulated disease control parameter values calculated by the simulation program. FIG. 6 shows a table 59 having identical structure to table 56. Table 59 illustrates a simulation in which the patient consumes 10 extra grams of carbohydrates at 8:00 and exercises for 60 extra minutes at 15:00. In this simulation, the differential $S_1(t)-O_1(t)$ is equal to 10 at 8:00 due to the 10 extra grams of carbohydrates consumed by the patient. Because scaling factor $K_1$ equals 4, the simulation program calculates simulated disease control parameter value $X(t_2)$ at time point 10:00 as 40 mg/dL higher than optimal control parameter value $R(t_2)$ at 10:00.

Similarly, the differential $S_3(t)-O_3(t)$ is equal to 4 at time point 15:00 due to the 60 extra minutes of exercise performed by the patient. With simulated disease control parameter value $X(t_4)$ exceeding optimal control parameter value $R(t_4)$ by 40 mg/dL at 15:00 and with scaling factor $K_3$ equal to -5, the simulation program calculates simulated disease control parameter value $X(t_5)$ at time point 18:00 as 20 mg/dL higher than optimal control parameter value $R(t_5)$.

FIG. 7 shows a graph 60 of the simulated disease control parameter values determined in table 59. Graph 60 is presented or displayed to the patient on screen 30 of the display unit.

Figures 8, 9:
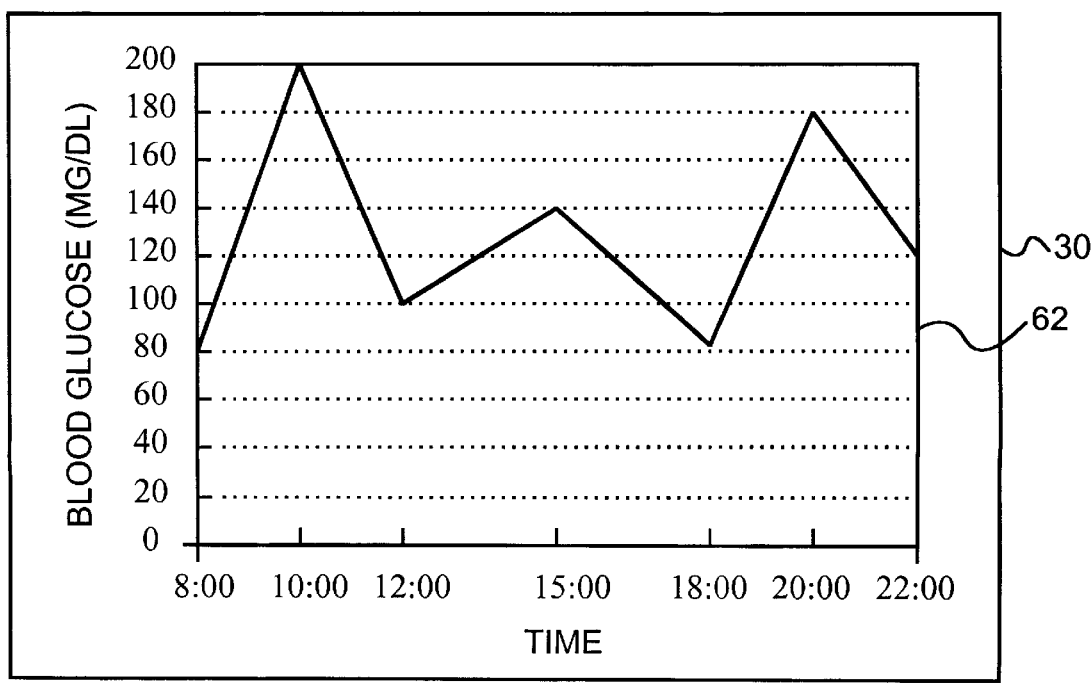
FIG. 8 is another table of values according to the invention.
FIG. 9 is a sample graph of disease control parameter values created from the table of FIG. 8.

FIGS. 8–9 illustrate a third example of simulated disease control parameter values calculated by the simulation program. Referring to FIG. 8, a table 61 illustrates a simulation in which the patient consumes 10 extra grams of carbohydrates at 8:00, injects 1 extra unit of insulin at 10:00, and exercises for 60 extra minutes at 15:00. The differential $S_2(t)-O_2(t)$ is equal to 1 at 10:00 due to the 1 extra unit of insulin injected by the patient. With simulated disease control parameter value $X(t_2)$ exceeding optimal control parameter value $R(t_2)$ by 40 mg/dL at 10:00, and with scaling factor $K_2$ equal to -40, the simulation program calculates simulated disease control parameter value $X(t_3)$ at time point 12:00 as equal to optimal control parameter value $R(t_3)$. FIG. 8 shows a graph 62 of the simulated disease control parameter values determined in table 61.

In addition to performing simulations with the simulation program, the patient records actual control parameter values and actual self-care values indicating actual self-care actions performed by the patient at each time point, step 218. These values are preferably recorded in recording device 38. Upon the patient's next visit to the healthcare provider, the actual control parameter values and actual self-care values are uploaded to provider computer 14, step 220. Those skilled in the art will appreciate that recording device 38 may also be networked to provider computer 14 through a modem and telephone lines or similar network connection. In this alternative embodiment, the actual control parameter values and actual self-care values are transmitted directly from the patient's home to provider computer 14.

In step 222, provider computer 14 adjusts scaling factors $K_M$ based on the difference between the actual control parameter values and the optimal control parameter values at each time point and the difference between the actual self-care values and the optimal self-care values at each time point. Scaling factors $K_M$ are adjusted to fit them to the actual patient data recorded. In this manner, the scaling factors are customized to the individual patient to enable the patient to run customized simulations. The new values of the scaling factors are stored on smart card 22 which the patient takes home and inserts in processor 24 to run new simulations.

FIG. 10 schematically illustrates the entry of parameter values (diet, medications, exercise, and disease control parameters) in recording device 38 of system 10.

FIGS. 11–12 illustrate another embodiment of the invention, in which the components of the simulation system are contained in a single stand-alone computing device 64. According to this embodiment, the system predicts each future disease control parameter value from an actual measured disease control parameter value (rather than from a prior simulated disease control parameter value, as discussed hereinabove with reference to FIGS. 1–10).

Referring to FIG. 11, computing device 64 includes a housing 66 for holding the components of device 64. Housing 66 is sufficiently compact to enable device 64 to be hand-held and carried by a patient. Device 64 also includes measuring device 40 for producing measurements of actual control parameters values, and a display 70 for presenting or displaying data to the patient. Device 64 further includes a keypad 68 for entering in device 64 the optimal control parameter values, the optimal self-care values, the patient self-care parameter values, the actual self-care parameter values, and the patient's physiological parameter values.

FIG. 12 shows a schematic block diagram of the components of device 64 and their interconnections. Device 64 has a microprocessor 72 and a memory 74 operably connected to microprocessor 72. Measuring device 40 and display 70 are also connected to microprocessor 72. Keypad 68 is connected to microprocessor 72 through a standard keypad decoder 78. Microprocessor 72 is connected to an input/output port 76 for entering in device 64 a simulation program to be executed by microprocessor 72, as will be explained in detail below.

Memory 74 stores the optimal control parameter values, the optimal self-care values, the patient self-care parameter values, the actual self-care parameter values $C_M(t)$, the scaling factors, and the patient's physiological parameter values. Memory 74 also stores the simulation program to be executed by microprocessor 72 and the indexes for calculating the scaling factors from the patient's physiological parameter values.

In the embodiment of FIGS. 11 and 12, microprocessor 72 is programmed to perform the functions performed by healthcare provider computer 14 in the embodiment of FIGS. 1–10. These functions include determining scaling factors $K_M$ from the patient's physiological parameter values. The functions also include adjusting scaling factors $K_M$ based on the difference between actual control parameter value $A(t_j)$ and optimal control parameter value $R(t_j)$, the difference between actual control parameter value $A(t_i)$ and optimal control parameter value $R(t_i)$, and the difference between actual self-care values $C_M(t_i)$ and optimal self-care values $O_M(t_i)$.

Figure 14:
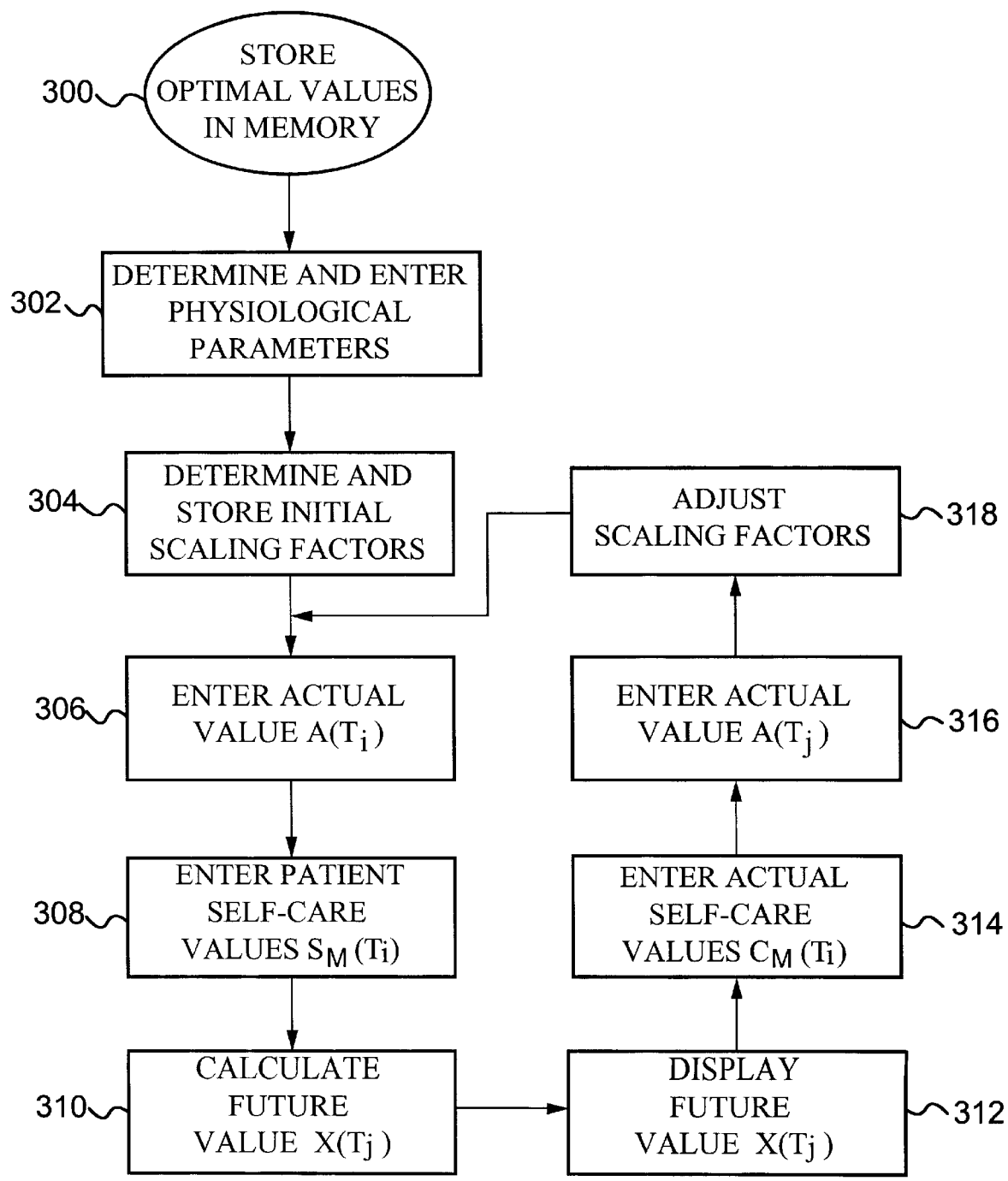
FIG. 14 is a flow chart illustrating steps included in another method of the invention.

FIG. 14 is a flow chart illustrating a preferred method of using the system of the second embodiment to predict an effect of patient self-care actions on a disease control parameter. In step 300, the optimal control parameter values and optimal self-care values are entered in device 64 and stored in memory 74. The optimal control parameter values and optimal self-care values may be entered in device 64 either through keypad 68 or through input/output port 76.

In step 302, the patient or healthcare provider determines the patient's physiological parameter values. The physiological parameter values are then entered in device 64 through keypad 68 and stored in memory 74. Following entry of the physiological parameter values, microprocessor 72 determines scaling factors $K_M$ from the indexes stored in memory 74, step 304. Scaling factors $K_M$ are then stored in memory 74. In an alternative method of determining and storing scaling factors $K_M$ in memory 74, scaling factors $K_M$ are determined in a healthcare provider computer, as previously described with reference to the embodiment of FIG. 13. Scaling factors $K_M$ are then entered in device 64 through keypad 68 or port 76 and stored in memory 74.

In step 306, the patient enters in microprocessor 72 actual disease control parameter $A(t_i)$. To enter actual disease control parameter $A(t_i)$, the patient places his or her finger on measurement device 40 (FIGS. 11, 12) at time $t_i$.

Measurement device 40 produces a measurement of actual disease control parameter $A(t_i)$ which is stored in memory 74. In step 308, the patient enters in microprocessor 72 patient self-care values $S_M(t_i)$ using keypad 68. In step 310, microprocessor 72 executes the simulation program stored in memory 74 to calculate future disease control parameter value $X(t_j)$.

The simulation program of the second embodiment (FIGS. 11, 12, 14) differs from the simulation program of the preferred embodiment (FIGS. 1–10, 13) in that, in the former, future disease control parameter value $X(t_j)$ is calculated from actual disease control parameter $A(t_i)$, rather than from a prior simulated disease control parameter value. In the second embodiment, future disease control parameter value $X(t_j)$ is calculated according to the equation:

$$X(t_j) = R(t_j) + (A(t_i) - R(t_i)) + \sum_M K_M(S_M(t_i) - O_M(t_i)) \quad (2)$$

Thus, future disease control parameter value $x(t_j)$ is determined from optimal control parameter value $R(t_j)$, the difference between actual disease control parameter $A(t_i)$ and optimal control parameter value $R(t_i)$, and the set of differentials between patient self-care values $S_M(t_i)$ and optimal self-care values $O_M(t_i)$. The differentials are multiplied by corresponding scaling factors $K_M$. Future disease control parameter value $X(t_j)$ is presented or displayed to the patient on display 70, step 312.

Once future disease control parameter value $X(t_j)$ is presented or displayed to the patient, the patient uses this value to select appropriate actual self-care actions to perform at time $t_i$. Alternatively, the patient may perform several more simulations of future disease control parameter value $X(t_j)$ to decide appropriate self-care actions to perform at time $t_i$. Once the patient has performed the self-care actions, the patient enters in microprocessor 72 actual self-care values $C_M(t_i)$ indicating the self-care actions performed, step 314. The actual self-care values are then stored in memory 74.

The patient also enters in microprocessor 72 actual disease control parameter $A(t_j)$ measured at time $t_j$. To enter actual disease control parameter $A(t_j)$, the patient places his or her finger on measurement device 40 at time $t_j$. Measurement device 40 produces a measurement of actual disease control parameter $A(t_j)$ which is stored in memory 74, step 316. In step 318, microprocessor 72 adjusts scaling factors $K_M$ based on the difference between actual control parameter value $A(t_j)$ and optimal control parameter value $R(t_j)$, the difference between actual control parameter value $A(t_i)$ and optimal control parameter value $R(t_i)$, and the difference between actual self-care values $C_M(t_i)$ and optimal self-care values $O_M(t_i)$. In this manner, the scaling factors are customized to the individual patient to enable the patient to run customized simulations. The new values of the scaling factors are stored in memory 74 and used by microprocessor 72 in subsequent simulations.

The invention presents a system and method for simulating a disease control parameter and for predicting the effect of patient self-care actions on the disease control parameter. According to a method of the invention, a future disease control parameter value $X(t_j)$ at time $t_j$ is determined from a prior disease control parameter value $X(t_i)$ at time $t_i$ based on an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$. In the preferred embodiment, the differentials are multiplied by corresponding scaling factors $K_M$ and the future disease control parameter value $X(t_j)$ is calculated according to the equation (1):

$$X(t_j) = R(t_j) + (X(t_i) - R(t_i)) + \sum_M K_M(S_M(t_i) - O_M(t_i)) \quad (1)$$

A preferred system for implementing the method includes an input device for entering the patient self-care values $S_M(t_i)$. The system also includes a memory for storing the optimal control parameter values $R(t_i)$ and $R(t_j)$, the prior disease control parameter value $X(t_i)$, the optimal self-care values $O_M(t_i)$, and the scaling factors $K_M$. A processor in communication with the input device and memory calculates the future disease control parameter value $X(t_j)$. A display is connected to the processor to present or display the future disease control parameter value $X(t_j)$ to a patient.

Virtual pet for patient self-care simulation

According to one embodiment of the invention, there is provided a system and method for simulating general health status and at least one disease control parameter, as determined, inter alia, by the effects of virtual patient self-care actions on a virtual patient. For the purposes of the present invention, the term "patient" includes a virtual patient, e.g., as displayed on a display of a virtual pet device.

The term "pet" as used herein includes a virtual pet, such as may be displayed on a virtual pet device of the invention. Such a virtual pet may be afflicted with a chronic disease or disorder, wherein the health status, at least one disease control parameter, the developmental state, and other characteristics of the virtual pet at any time point may be displayed on a display of a virtual pet electronic device.

The terms "patient self-care parameter" and "patient self-care parameter values" include virtual self-care parameter values applicable to a virtual pet and entered by an owner of the virtual pet or virtual pet device. The term "pet owner" includes persons taking care of a virtual pet or persons operating a virtual pet device.

The terms "prior disease control parameter value" and "future disease control parameter value" as used herein include a first or earlier virtual disease control parameter value and a second or later virtual disease control parameter value, respectively.

Figure 15:
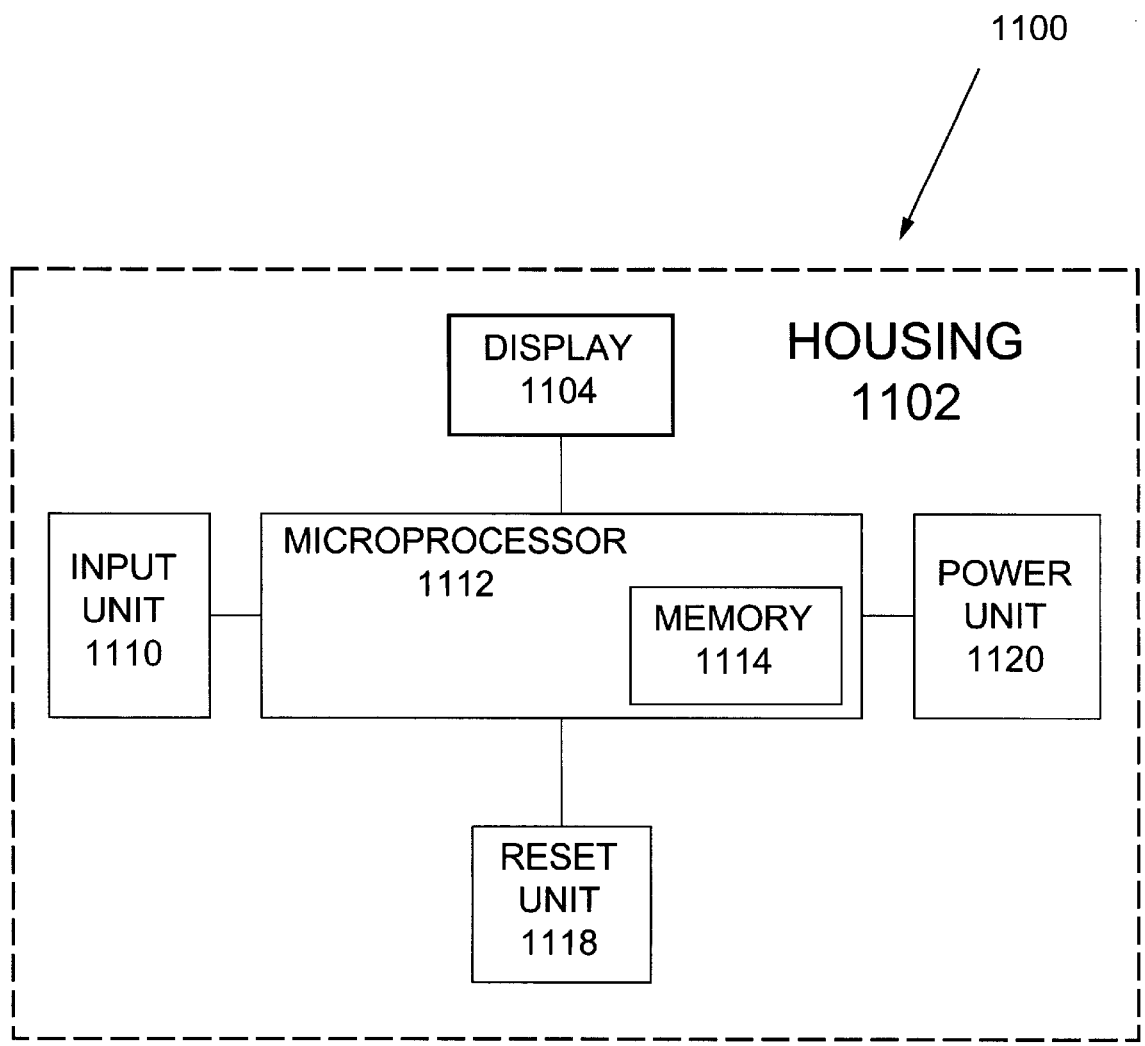
FIG. 15 is a schematic block diagram of a virtual pet device according to another embodiment of the invention.

FIG. 15 shows a simple block diagram representing components of a virtual pet device 1100 according to the invention. Virtual pet device 1100 includes a microprocessor 1112 having a memory 1114, an input unit 1110, a reset unit 1118, a power unit 1120, a housing 1102, and a display 1104 integral with housing 1102. Microprocessor 1112 is connected directly to each of: input unit 1110, reset unit 1118, power unit 1120, and display 1104.

Device 1100 may further include an audio unit 1122 (FIG. 17) for providing a source of sound. Sounds generated by device 1100 may include those synchronized to and coordinated with various graphics, as well as an alarm to warn a pet owner of the time with respect to a scheduled self-care or medical regimen related event. For example, device 1100 may include a Pulmozyme™ alarm unit or function which signals each scheduled administration of Pulmozyme™. The audio unit may also provide a plurality of tones which collectively provide a musical tune from device 1100. Device 1100 further includes a clock unit or feature (not shown) synchronized to real time.

A plurality of icons may be displayed on display 1104, as will be described fully hereinbelow. Input unit 1110 may include a plurality of buttons or input controls 1110' for selecting from the plurality of icons and for inputting data to device 1100, as will also be described fully hereinbelow. Power unit 1120 supplies power, e.g., via a photoelectric or photovoltaic unit, or via a suitable battery mounted within housing 1102, as is well known in the art. Reset unit 1118 preferably includes a recessed control located at the rear of device 1100 such that it cannot be activated inadvertently. Activating reset unit 1118 serves to reset various functions of device 1100, e.g. clock, alarm, and resets the developmental state of a virtual pet to time zero, as will be more fully appreciated from the following description.

Device 1100 may further include a night-light unit or feature (not shown) wherein a relatively low level of light is emitted, e.g., from display 1104. Such a night-light can be activated via one or more of controls 1110', and provides additional ambient light in a child's bedroom, and at the same time greatly facilitates locating device 1100 under conditions of low ambient light intensity.

Figure 16:
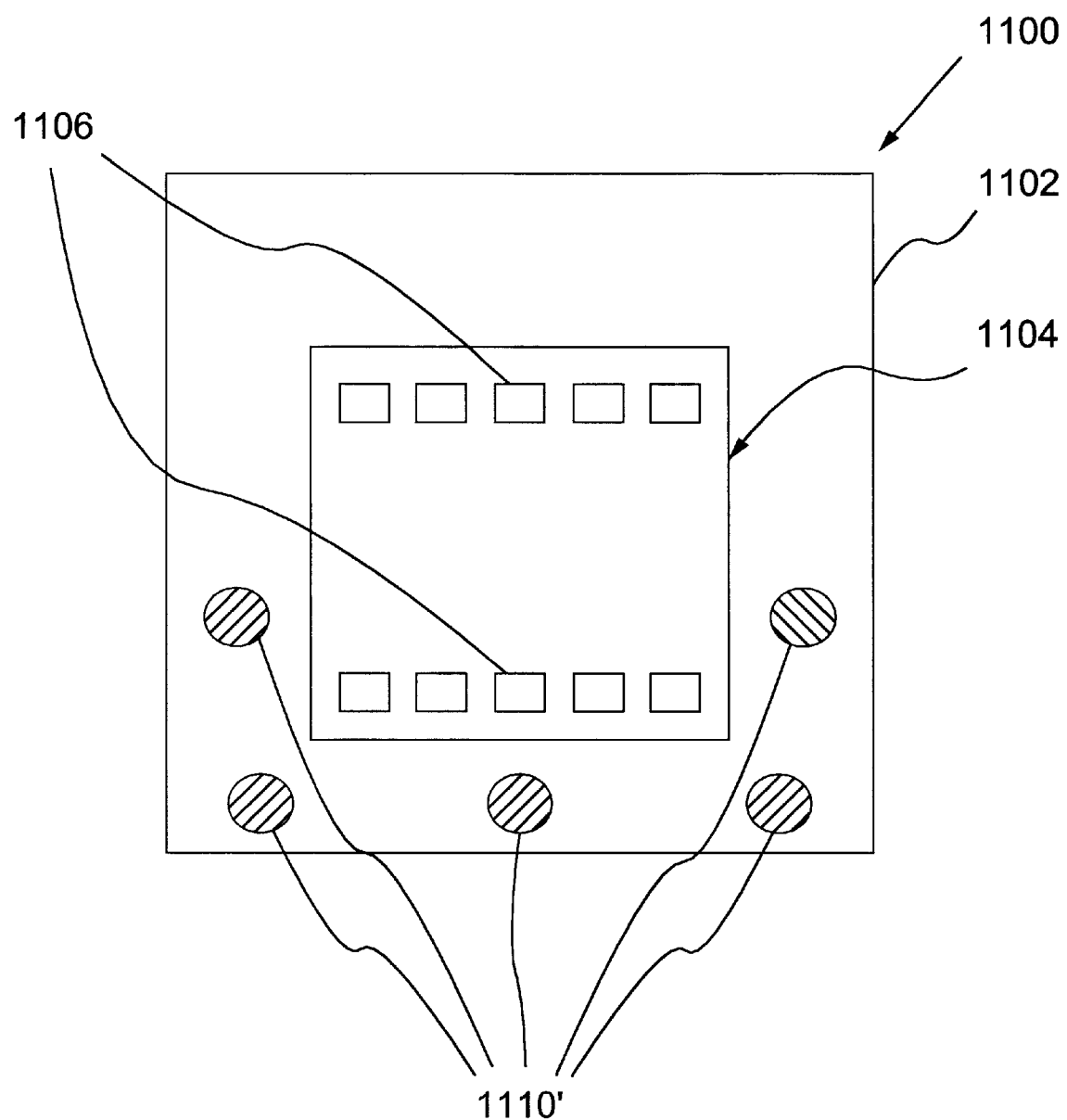
FIG. 16 shows a schematic representation of a virtual pet device according to one embodiment of the invention.

A preferred embodiment of a virtual pet device 1100 of the present invention is shown in FIG. 16. Device 1100 includes housing 1102 and display 1104 integral with housing 1102. A plurality of icons 1106 are shown at the top and bottom of display 1104. A plurality of input controls 1110', e.g. a total of 5, provide input means which may be mounted externally on housing 1102, preferably around display 1104. Different numbers of controls 1110' and different arrangements of the plurality of controls other than those shown in FIG. 16 may be used within the scope of the invention. Housing 1102 and controls 1110' may each be made of various materials such as (without limitation) ceramics, wood, or plastics, including opaque, transparent, translucent, colored or colorless plastic materials.

Device 1100 is preferably relatively small and lightweight such that it can be safely and readily carried by a small child. The overall dimensions of device 1100 are large enough to accommodate the features of device 1100 described herein, and small enough to be readily transported by a small child.

Display 1104 is preferably a liquid crystal display, having dimensions large enough to display those features specified herein and small enough to be accommodated by device 1100. A preferred resolution of display 1104 is 36×24 pixels.

The virtual pet device of the present invention, is adapted such that various embodiments are suitable for both genders (boys and girls). Owners of the pet may or may not suffer from a congenital or chronic medical condition. The device of the present invention is particularly suited to children in the age range of 5–12 years.

According to one embodiment of the invention, virtual pet device 1100, is programmed such that the virtual pet to be displayed on display 1104 is a puppy which initially hatches from an egg, lives in an accelerated timeframe (preferably from about 8 to about 10 times faster than real time), and has the potential to mature in about one year of the pet's accelerated timeframe. Thus a well cared for virtual puppy of the invention can mature in the space of a few weeks.

According to one embodiment of the invention, virtual pet device 1100 provides a toy, wherein it is the owner's responsibility to ensure that the virtual pet of the device remains healthy, gains weight, goes to school, and ultimately graduates. In particular, it is the responsibility of the owner or operator of the toy to care for the virtual pet by inputting self-care parameter values. The device is programmed such that these objectives can be achieved by entering suitable self-care parameters related to a particular medical condition afflicting the virtual pet. For example, in the case of cystic fibrosis (CF) the owner of the virtual pet must enter data into the device concerning virtual medications administered (e.g., Pulmozyme™, bronchodilators, oral antibiotics), chest physical therapy undertaken, physical exercise undertaken, and nutrition provided, as well as health risks (sneezers and smokers) avoided. Further information concerning medications administered and health risks to be avoided are provide hereinbelow under the description of a medical regimen for CF, as well as under the Example provided.

Data which may be entered into device 1100 includes patient self-care values, nutrition related values, and risk factor values. The term "values" as used in the context of data entered into device 1100 includes any kind of data entry relating to patient self-care, patient life-style/risk avoidance, and/or relating to a medical regimen for a disease of an actual patient or a real patient. Information on a recommended medical regimen for a particular disease or disorder may be supplied with the device.

Although a virtual pet of the present device 1100 "lives" in an accelerated timeframe, some of the activities of the virtual pet are synchronized to real time. For example, the pet may sleep each night at approximately the same time and for the same period as its owner, and medications may be administered at a frequency synchronized to real time (i.e. medications specified as being once daily are administered once in each 24 hr. period of real time).

Virtual pet device 1100 includes graphics of the virtual pet which change over time as the pet grows and develops (e.g. into a dog). Graphics may include expressions of ill health or good health, such as a happy face, a sad face, or an ambulance, etc. as is described in further detail hereinbelow.

Input unit 1110 of the present invention, e.g. buttons or controls 1110', may be used to enter values relating to self-care parameters: e.g., Pulmozyme™ usage, pancreatic enzyme usage, bronchodilator usage, antibiotic usage, physical exercise taken, chest physical therapy, caloric intake, vitamin supplements taken, exposure to smokers, and exposure to sneezers.

Microprocessor 1112 of the present invention includes means for determining scaling factors $K_M$ from values entered for patient self-care parameters: e.g., Pulmozyme™ usage, pancreatic enzyme usage, bronchodilator usage, antibiotic usage, physical exercise taken, chest physical therapy, caloric intake, vitamin supplements taken, exposure to smokers, and exposure to sneezers.

According to a preferred embodiment of virtual pet device 1100, determination of a future disease control parameter value $X(t_j)$ at time $t_j$ of the virtual pet from a prior disease control parameter value $X(t_i)$ at time $t_i$ is performed essentially as described hereinabove with reference to FIGS. 1–10. That is to say the determination is based on: an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$. The differentials may be multiplied by corresponding scaling factors $K_M$ and the future disease control parameter value $X(t_j)$ is calculated according to the following equation (1):

$$X(t_j) = R(t_j) + (X(t_i) - R(t_i)) + \sum_M K_M (S_M(t_i) - O_M(t_i)) \qquad (1)$$

According to one embodiment of the invention, device 1100 for simulating general health status and at least one disease control parameter includes input unit 1110 for entering the patient self-care values $S_M(t_i)$. The system also includes memory 1114 for storing the optimal control parameter values $R(t_i)$ and $R(t_j)$, the prior disease control parameter value $X(t_i)$, the optimal self-care values $O_M(t_i)$, and the scaling factors $K_M$. Microprocessor 1112, in communication with input unit 1110 and memory 1114, calculates the future disease control parameter value $X(t_j)$. Display 1104, connected to the microprocessor 1112, displays the future disease control parameter value $X(t_j)$ to an owner of device 1110, a patient, or other individual.

Cystic Fibrosis Medical Regimen

For the purpose of the present invention, a typical medical regimen for a patient or virtual patient with cystic fibrosis may include: administration of various medications; physical therapy and exercise; risk avoidance; nutrition; self-monitoring, e.g., of disease control; and interaction with health care providers. With reference to medications administered, the following are recommended once per day: Pulmozyme™, a bronchodilator, and antibiotics (oral). Pulmozyme™ is a genetically engineered drug manufactured and distributed by Genentech Inc., South San Francisco, Calif. It liquefies much of the thick mucous that builds up in the lungs of cystic fibrosis patients. It is inhaled once per day using a nebulizer device which is connected to a small air compressor. The patient normally spends several minutes deeply inhaling the drug.

In addition to the above medications, pancreatic enzymes are taken before meals (with additional amounts of pancreatic enzymes being taken for high fat food). Chest physical therapy (CPT) is recommended twice per day, and may be selected through the CPT icon of the virtual pet device. Physical exercise is recommended to be entered (i.e. virtual exercise to be performed by the pet), several times per day, and may be entered via the PLAY icon of the pet device.

A medical regimen for cystic fibrosis may include avoidance of certain risk factors, e.g., people with respiratory diseases ("sneezers") and people who smoke ("smokers"). Another possible risk factor to be avoided is heat exposure. A medical regimen for cystic fibrosis may further include various nutritional factors, such as adequate caloric intake, vitamin supplements, and salt supplement.

A cystic fibrosis patient can expect to interact with health care providers on a routine basis for a periodic check-up (e.g. quarterly), at which time the patient's body weight and lung function can be determined (the latter via a spirometer). Unscheduled interaction with health care providers may also occur, e.g., during periods of hospitalization. Such hospital visits may be precipitated by situations such as poor lung function, excessive weight loss, fatigue, etc.

Patient self-care parameter values, based on a recommended or ideal medical regimen, may be entered into device 1100 via one or more of the plurality of controls 1110' e.g., from a listing of options displayed on display 1104. In the case of cystic fibrosis, a plurality of patient self-care parameters have been presented hereinabove. Disease control parameters in the case of cystic fibrosis include lung function and body weight. A general health status of the virtual pet may be determined from a weighted value of each of the disease control parameters, and presented on the display for the benefit of the pet owner. The general health status of a virtual pet may be represented as a Total Score which may be displayed on the display as a numerical value. In this case, care of afflicted virtual pets can become competitive and take the form of a game in which each child (owner of a virtual pet) attempts to obtain the highest Total Score for the general health status of his/her virtual pet. The use of such a game may be useful in enhancing interest in device 1100 and motivation towards compliance with a medical regimen.

According to one embodiment of the invention, virtual pet device 1100 may include a communications means (not shown), operably coupled to microprocessor 1112 for connection of device 1100 to a computer, network, or to another device, such as a medical measurement device. Such a communications means may utilize wireless communications such as infrared or radio frequency radiation, or may be in the form of a connector mounted externally on housing 1102. Optionally, a modem circuit (also not shown) may be coupled between the communications means and microprocessor 1112.

Figure 17:
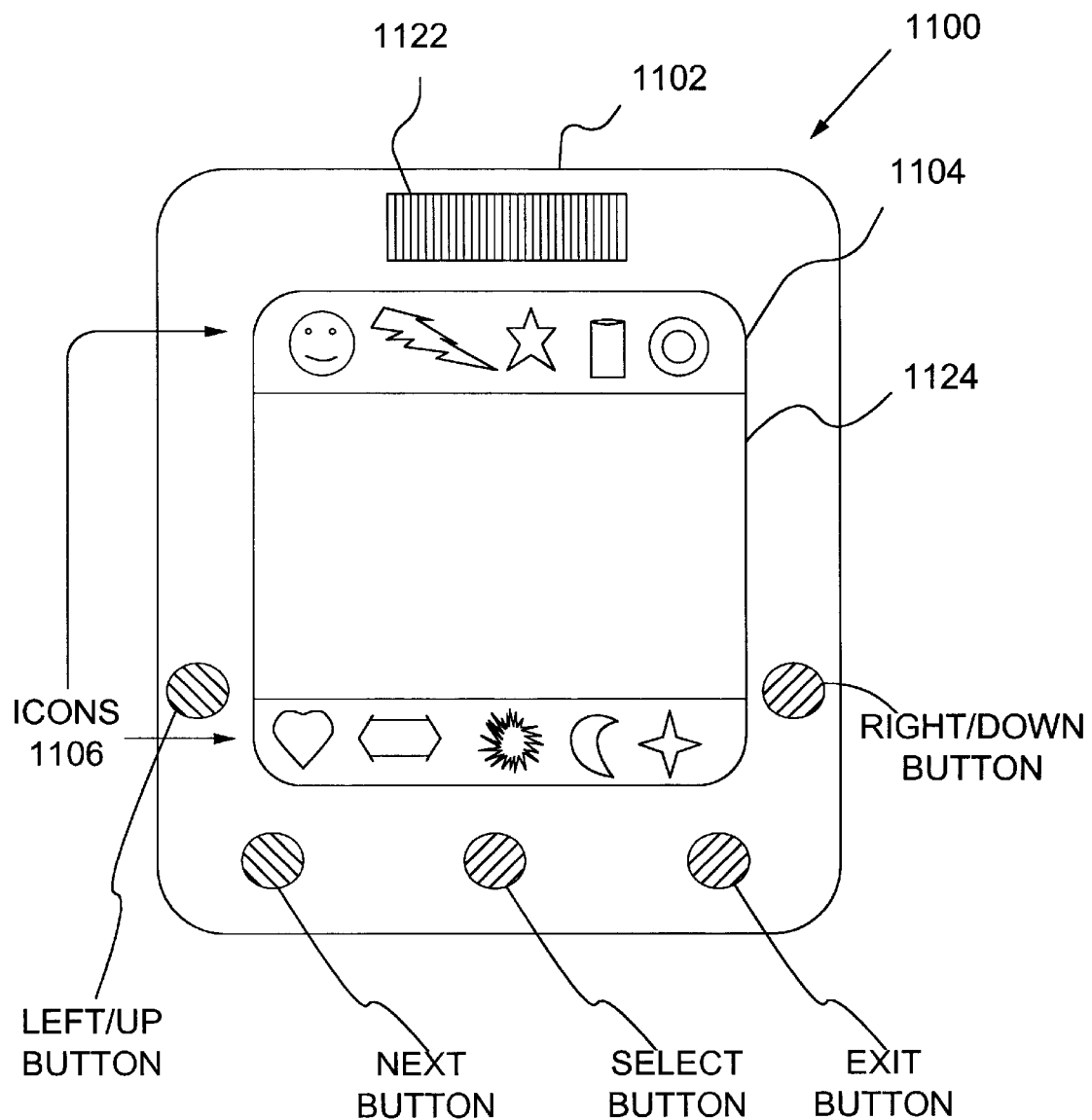
FIG. 17 shows a virtual pet device adapted for cystic fibrosis patients according to the invention.

A currently preferred embodiment of virtual pet device 1100 of the invention, as shown in FIG. 17, will now be described according to the following example.

EXAMPLE

A. Introduction

FIG. 17 shows virtual pet device 1100 adapted for cystic fibrosis patients. Device 1100 is particularly suitable for children aged 5–12. Device 1100 is useful in improving pediatric cystic fibrosis patients' adherence to the CF medical regimen. The device of FIG. 17 also serves to reinforce the importance of school graduation, and to increase communication about cystic fibrosis between the patient, the patient's family and friends, and health care providers. The icons shown in FIG. 17 are just placeholders, that is to say, icons in a virtual pet product according to the invention may not be precisely as shown.

Virtual pet device 1100 includes display 1104 (for example, a liquid crystal display). The size of housing 1102 or exterior plastic case is approximately 48 mm by 60 mm by 18 mm (1.9×2.4×0.75 in.) Five controls 1110' on the front of device 1100 allow the owner to control the functions of device 1100. Device 1100 includes a night-light feature which may be activated by the LEFT/UP button. On the back of device 1100 is a reset button, as well as a battery door retained by two screws. A replaceable, model 2032 battery powers device 1100 for 4 months. A quick-release key chain (not shown) may be attached to device 1100.

The exterior plastic case and buttons 1110' can be chosen from a variety of colors. The plastic case can be transparent. Small decals or printing can be placed on the front of device 1100 for branding purposes as well as for identification of buttons 1110'.

The device of FIG. 17 includes a slightly larger and higher resolution LCD than is generally found in prior art devices of this type. The physical size of the LCD is 31 mm by 26 mm, and the resolution of the main animation part of the display is 36×24 pixels. There are five icons above and five icons below a main animation display 1124.

B. Objectives and Rationale

Device 1100 does not intend to be a substitute for the active involvement of the CF care team. Instead, it is intended to be an educational and motivational supplement to their efforts.

The primary objective of device 1100 is to improve compliance in cystic fibrosis patients ages 5–12. In general, improved compliance may be accomplished through increased knowledge and/or increased motivation to comply. The product described herein is more concerned with increasing motivation, and expends relatively little effort to explicitly increase the patient's knowledge about their CF regimen.

Device 1100 primarily improves motivation by increasing the patient's sense of self-mastery (self-efficacy) through repeated success in managing the CF regimen of their virtual pet. The patient experiences the consequences of their care efforts in an exaggerated manner in an accelerated timeframe. The results of both compliance and non-compliance can be rapidly seen in the health of their virtual pet (e.g., via graphics, Total Score, etc.). Virtual pet care consequences can develop in minutes or hours that would take weeks or months in the patient's real world. This experience assists patients in developing positive beliefs and expectations about assuming responsibility for their own self-care and treatment.

Studies have shown that involving children in their own care results in increased compliance to their treatment regimen, increased patient satisfaction with treatment, increased feeling of control, increased sense of competence and independence, and most importantly improved health, reduced clinical utilization, and reduced care costs.

Other aspects of the use of device 1100 that contribute to improved motivation are: increased sense of normalcy, improved communication between patient and health care providers and patient and family. The use of device 1100 by non-patients (peers and family members) improves their ability to identify with the CF regimen requirements.

C. Target Audience a) Device 1100 is particularly targeted to children aged 5–12 years having unspecified state of health.

D. Story Line

It is the responsibility of the owner to care for their virtual pet (named "Pawz, the Pulmozyme Puppy™") so that it graduates from school and develops into a healthy adult. The device of this Example extends the concept of virtual pet care found in prior art virtual pets in that, in this instance the pet ("Pawz") has the disease cystic fibrosis, and the owner must perform additional disease-related or medical regimen-related activities to successfully care for the pet.

Pawz is initially hatched from an egg. As a puppy, Pawz has cystic fibrosis. It is the owner's responsibility to care for Pawz to ensure that Pawz remains healthy, gains weight, goes to school, and ultimately graduates from veterinary school.

The owner must properly administer Pawz' medications, monitor key health functions, perform chest physical therapy, undertake exercise, avoid certain health risks, provide adequate nutrition, and seek proper health care when necessary.

Additionally, the owner needs to play with Pawz, make sure he goes to school, and make sure he gets enough sleep. If Pawz does not attend school adequately, he will not graduate. Pawz changes graphics as he grows. Expressive graphics indicate health status; tummy ache, sad face, etc.

Numerical values and bar graph representations of general health, body weight, and lung function are displayed in the health status section of device 1100. Additionally, an overall score (Total Score) can be displayed in the health status section as an incentive for the patient to replay the "game" to achieve higher scores (as detailed below).

Pawz lives in an accelerated timeframe, about 8 to 10 times faster than ours. Pawz is also a dog and can mature in about one year in his timeframe. A well cared for Pawz takes about one human month to mature and graduate from school. Although Pawz lives in an accelerated timeframe, some of his activities such as sleep and medications are synchronized to real time. In other words, Pawz sleeps at night when the patient sleeps. Also Pawz takes daily medications, such as Pulmozyme™, only once per day in real time.

The owner's name can be input into device 1110 for the purpose of identification. The owner can select which of various medications their pet should take on a regular basis. Medications available include Pulmozyme™, pancreatic enzymes, bronchodilators, and oral antibiotics. For example, if the owner disables Pulmozyme™, then Pulmozyme™ does not appear on the MEDICATION menu during OPERATION of device 1100.

Device 1100 includes a daily Pulmozyme™ alarm that can be set by the owner of device 1100, and which may be used to alert a CF patient to the patient's scheduled time to administer their real-world Pulmozyme™.

Device 1100 also includes a MUTE function which turns off the sound feature, e.g. via audio unit 1122, as well as a PAUSE function which is activated when the operator of device 1100 selects the SCHOOL icon.

E. Medical Regimen for Pawz, the Pulmozyme Puppy™

1. Medications

The following medications may be sequentially displayed when the patient first selects the MEDICINE icon and then presses the MODE button.

a) Pulmozyme™—recommended once per day b) Pancreatic enzymes—to be taken before a meal, extra amounts are to be taken for high fat food.

c) Bronchodilators—recommended once per day d) Oral antibiotics—recommended once per day.

In addition to the above, inhaled antibiotics and intravenous antibiotics may be included in certain embodiments of device 1100. Additional medications can be included for specific embodiments of the invention.

While a particular medicine is selected on the LCD, the selected medicine is virtually administered to the pet when the pet owner presses the ENTER button. A particular medicine only appears if it is currently enabled by the patient.

2. Self-monitoring

After the patient selects the HEALTH status icon, the following are displayed sequentially when the patient presses the MODE button.

a) Total Score, which represents progress towards graduation and general health—3 digits (1–999)

b) Weight—2 digits (1–99)

c) Lung function—2 digits (1–99)

d) Happiness—2 digits (1–99)

e) Hunger—2 digits (1–99)

2. Physical Therapy/Exercise b) Chest physical therapy (CPT)—selected through the CPT icon. The recommended frequency of CPT is twice per day.

c) Physical exercise—selected through play activities.

The recommended frequency of physical exercise is several times per day.

In addition to the above, use of postural drainage, a flutter device, and/or a vibrating vest may be included in certain embodiments of device 1100.

2. Risk Avoidance a) Sneezers—the pet is to avoid on-screen sneezer characters and jump on them.

b) Smokers—the pet is to avoid on-screen smoker characters and jump on them.

In addition to the above, avoidance of exposure to heat may be included as a risk factor in certain embodiments of device 1100.

3. Nutrition b) Adequate caloric intake by the pet is required—ingestion of Food/Calories is selected via the FOOD icon.

c) Vitamin supplements—this function of pet nutrition is similarly selected via the FOOD icon. In addition to the above, a salt supplement may be included as a nutrition factor in certain embodiments of device 1100.

2. Interaction with Health Care Providers (HCP's)

b) Hospitalization—a visit to hospital may be initiated as a result of one or more of the following conditions experienced by the pet of device 1100:
  i. excess weight loss
  ii. poor lung function After a hospital visit, health of the pet is restored to a good level, corresponding to a general health status score or Total Score within a desired range.

a) Quarterly checkup—during this periodically scheduled procedure the following disease control parameters are evaluated:
  i. lung function (Spirometer)
  ii. body weight F. Games The first two listed games may be documented in the instructions on how to operate device 1100 and to care for the pet, and they appear in the GAMES menu. Three additional games are "Easter Eggs" (refer to section G. hereinbelow) and are initially undocumented and do not appear in the GAMES menu. The three additional games will only be revealed through a newsletter for owners of device 1100 belonging to a club known as Club Pulmozyme™.

a) Bouncing Ball Catch (The aim of this game is for the pet to catch a ball that randomly appears from the right edge of the LCD.)

b) Follow Me (The aim of this game is to match the audio tone sequence of device 1100.)

G. Undocumented Features (Easter Eggs)

In order to sustain long-term interest in device 1100, information about new games to be included in device 1100 may be released to owners through periodical publications (Club Pulmozyme™ newsletter). Examples of additional games are: a) Rock, Scissors, Paper; b) Flying; c)Jump On Enemy. Further information on these games is provided under section M., below.

New games may be accessible in the GAMES menu, but only by entering a special key sequence. (For example pushing LEFT RIGHT RIGHT RIGHT buttons could cause the Rock, Scissors, Paper game to play.)

H. Other Features of Pawz

Features of device 1100 according to the current Example include the following:

a) Entry of owner's name b) Pulmozyme™ Alarm clock c) Mute function d) Pause function Additional features of device 1100 may be included in other embodiments of the invention, e.g., a record of the owner's Pulmozyme™ usage.

F. Graphics Indicating Health Status

Graphics representing the pet or activities associated with the pet may include the following.

a) Tummy ache b) Coughing c) Slow running d) Sad face e) Ambulance

F. Disease Simulation System

Two principal disease control parameters are simulated in device 1100: lung function and body weight. Lung function is increased or improved by appropriate and timely applications of Pulmozyme™, bronchodilators, oral antibiotics, chest physical therapy, and exercise. Lung function is decreased through non-compliance with the medical regimen, as well as through exposure to sneezers and smokers.

Body weight is increased by adequate food and vitamin supplement intake, together with properly timed administration of pancreatic enzyme(s).

Values for Total Score and Happiness are based on a combination of the above factors, plus the amounts of play and interaction with the owner.

Reduction in general health results in slow running speed, need for more sleep, general expressions of unhappiness, and, if untreated, a trip by ambulance to the hospital. Such signs of poor health are represented graphically on animation display 1124.

K. Liquid Crystal Display (LCD)

The display 1104 includes 5 icons at the top and 5 icons at the bottom of the screen. The central part of display 1104 comprises animation display 1124 in the form of a 36×24 pixel map on which the animated graphics and text are displayed.

The top five icons are from left to right: HEALTH STATUS, FOOD, MEDICINE, CHEST PHYSICAL THERAPY (CPT) and SHOWER. The bottom five icons are from left to right: GAMES, SCHOOL, PRAISE, SLEEP, and NEEDS ATTENTION.

L. Buttons/Controls

There are five controls on the front face and a RESET button on the back. The front control buttons include:
 a) LEFT—generally move left or up. This button also activates (lights up) the night light
 b) RIGHT—generally move right or down
 c) NEXT—moves to next icon or menu item
 d) SELECT—selects current icon or menu item
 e) EXIT—exits current process L. Device Functions After activating the RESET control, or after insertion of a NEW BATTERY the series of events is as follows:
 a) Set Clock
 b) Set Alarm
 c) Input Patient Name (Up to 6 letters per line, 2 lines)
 d) Select medication to be given to Pawz.
 e) Then Pawz is hatched
 f) Then device 1100 enters NORMAL MODE NORMAL MODE—No icon is selected; in this mode Pawz is developing.

Owners can press the NEXT button to sequentially highlight each of the 10 icons. When a particular icon is highlighted and the owner presses the SELECT button, then the process corresponding to that icon begins.

When none of the icons are highlighted, the owner can press the SELECT button to go to the CLOCK/MISCELLANEOUS process.

Main Processes

The Main Processes are as follows:

I. Clock/Miscellaneous Process (The NEXT button cycles through the following menus. The SELECT button initiates Set function. The EXIT button exits.)
 i) Display/Set Clock
 ix) Display/Set Alarm
 x) Display/Set Patient Name
 xi) Display/Set Use of Pulmozyme
 xii) Display/Set Use of Pancreatic Enzyme
 xiii) Display/Set Use of Bronchodilator
 xiv) Display/Set Use of Oral Antibiotics II. Health Status Icon Process (The NEXT button cycles through the following displays. The EXIT button exits.)

Each display contains a large icon for the value, a bar graph display, and a two or three digit numeric value. When the display comes on the bar graph extends, the numerals count up, and an audio tone is generated, stepping up in increasing frequency.
 a) Total Score—(Icon=Graduation Cap)—represents progress towards graduation and general health. 3 digits (1–999). The name of Pawz' current state is shown (4 to 8 characters indicating 1 of 15 states.)
 b) Weight—(Icon=Scale) 2 digits (1–99)
 c) Lung function—(Icon=Lungs) 2 digits (1–99)
 d) Happiness—(Icon=heart) 2 digits (1–99)
 e) Hunger—(Icon=Apple) 2 digits (1–99)

III. Food Icon Process (The NEXT button cycles through the following menus. The SELECT button initiates eating sequence, which when complete exits back to NORMAL MODE. The EXIT button exits back to NORMAL MODE.)

Pawz is shown with the FOOD icon. When a food item is selected, Pawz eats it in three bites. Food items are as follows:
 a) ice cream cone
 b) apple
 a) chicken leg
 b) pizza slice
 c) vitamin supplement IV. Medicine Icon Process (The NEXT button cycles through the following menus. The SELECT button initiates taking the medicine sequence, which when complete exits back to NORMAL MODE. The EXIT button exits back to NORMAL MODE.)

Pawz is shown with the MEDICINE icon. When a medicine item is selected, Pawz uses it in three small animations. If the patient has turned off a medicine item, it does not appear in this menu cycle. If Pawz has already been given his daily medication and the owner tries to administer more, Pawz shakes his head left to right and refuses to take it. The following medicine items are included:
 a) Pulmozyme™—recommended use once per day
 b) Bronchodilators—recommended use once per day
 c) Oral antibiotics—recommended use once per day
 d) Pancreatic enzymes—must be taken before a meal; extra must be taken for high fat food V. Chest Physical Therapy Icon Process Pawz is shown in a prone position. A hand icon pounds on his back three times. Then the device returns to NORMAL MODE.

VI. Shower Icon Process

A spray of water appears and any debris on the ground disappears. Then the device returns to NORMAL MODE.

VII. Games Icon Process (The NEXT button cycles through the following menus. The SELECT button initiates the game, which when complete stays in GAMES Icon Process. The EXIT button exits back to NORMAL MODE.)
 a) Bouncing Ball Catch—(The aim is for Pawz to catch a ball randomly "thrown" in from the right edge of the display.) A player moves a graphic of Pawz up or down to catch a ball before it goes past Pawz. Balls gradually speed up. The game ends when Pawz misses a ball. One point is scored for each caught ball.
 b) Follow Me—(The aim is to match the audio tone sequence of the device.) One audio tone is generated and one of five buttons indicated to be pushed to match it. A player must then push the button indicated. If the player correctly pushes a button to match the sequence, then one more tone is added to the sequence. The game ends when the player enters an incorrect sequence. One point is scored for each correct sequence.

Undocumented Games (Easter Eggs)

In order to sustain long-term interest in device 1100, the company will release information about new games found in device 1100 to the owners through the quarterly Club Pulmozyme™ newsletter. These new games are accessible in the usual PLAY menu, but only through a special key sequence.

a) Rock, Scissors, Paper—The player or owner must push one of three buttons to select rock, scissors, or paper. Then Pawz shows his selection. Game lasts for five turns. One point is scored for each time the player beats Pawz. (Rock beats scissors; paper beats rock; scissors beats paper.)

b) Flying Game—A player moves Pawz up and down to dodge oncoming objects scrolling in from the right edge. The game continues until Pawz is hit. One point is scored for each object successfully dodged.

c) Jump On Enemy—Enemy objects move in from the right side of the display. A player maneuvers Pawz left and right and times Pawz' jump to land on top of an enemy object. The game ends when an enemy touches Pawz. One point is scored for each enemy squashed.

VIII. School Icon Process

Pawz is shown flipping the pages of a book. This is an essential part of Pawz' upbringing. Pawz does not demand any interaction with the owner (e.g. actual patient) when in this mode, so it is equivalent to the PAUSE function. This process ends when the EXIT button is pressed and the device goes back to NORMAL MODE.

IX. Praise Icon Process

If Pawz is feeling sad, the activation of the PRAISE function, occasionally, makes him feel better. If Pawz feels better he might get a happier face; or some small hearts might appear next to Pawz; or Pawz might dance to a melody.

X. Sleep Icon Process

When Pawz goes to sleep, letter "Z"s are displayed above his head. During the night period (real time) sleep is essential to Pawz' wellbeing. He may also need to take naps during the day. After Pawz begins to sleep, device 1100 returns to NORMAL MODE.

XI. Needs Attention Icon Process

This is not a player/owner selectable icon. When device 1100 want to alert the player that Pawz needs attention, it beeps, and highlights this icon. The player must then push the NEXT or SELECT button to select some other process. NEEDS ATTENTION occurs when Pawz is in bad health or under threat from sneezers or smokers sneaking up on Pawz. The owner/player should address Pawz health problems or jump on sneezers and smokers.

Other Items a) AMBULANCE TO HOSPITAL If the health of Pawz deteriorates below a minimum level, an ambulance graphic appears on the LCD to take Pawz to hospital. Pawz then undergoes treatment leading to restoration of health to a good level.

b) REGULAR CHECKUP—Periodically, Pawz goes to the doctor for a periodic checkup. Device 1100 beeps for attention and text on the screen says "GO TO CHECKUP". Any button initiates a sequence where Pawz is weighed and lung capacity is measured. A happy melody is played, Pawz dances, then device 1100 returns to NORMAL MODE.

c) TUMMYACHE—If Pawz eats without taking pancreatic enzymes, then he gets a tummy ache, indicated by lightning bolts by the stomach.

d) COUGHING—If Pawz' lung capacity declines he coughs. Coughing is indicated by beeping and lightning bolts coming out of the mouth of the pet. If Pawz' lung capacity declines further, an additional consequence is a decline in Pawz' movement speed.

e) MELODY—Device 1100 can reproduce 14 notes (some melodies/songs are included).

L. Graphics

There are graphics for 15 different variants of Pawz developed for device 1100 to represent various states and/or developmental stages. Each Pawz variant has expressions indicating general status as well as animations necessary for all activities, including games.

Virtual pet device 1100 is described herein primarily with respect to a puppy having cystic fibrosis. However, it will be readily apparent to one skilled in the art that the device of the present invention could equally feature other animals/pets afflicted with other diseases/disorders.

SUMMARY, RAMIFICATIONS, AND SCOPE

Although the above description contains many specificities, these should not be construed as limitations on the scope of the invention but merely as illustrations of the presently preferred embodiment. For example, although the virtual pet device embodiment has been described primarily with respect to cystic fibrosis, the invention may also be applied to other chronic disorders and diseases.

In one embodiment, the invention may be implemented as a simulation system for educating and training patients, family members, peers, and/or health care personnel in predicting the effect of medical regimen adherence and/or self-care actions and risk avoidance on one or more disease control parameters of a chronic disease or on-going medical condition.

In one embodiment of a simulation system of the invention, in the context of the control of blood glucose levels in diabetes, the insulin dose values are representative of simulated insulin doses and the blood glucose values are representative of simulated blood glucose concentrations. The patient enters various insulin dose values and blood glucose values in the simulation system to learn their effect on his or her future blood glucose concentration.

In alternative embodiments, the apparatus may store guidelines for parameters or factors related to diet, exercise, and other therapy parameters. Further, the apparatus may be programmed to prompt a patient for data relating to the therapy parameters and to display recommended guidelines to the patient.

Therefore, the scope of the invention should be determined not by the examples given but by the appended claims and their legal equivalents.

What is claimed is:

1. A system for providing simulated disease control parameter values for at least one disease control parameter of a chronic disease, said system comprising a freely transportable virtual pet device including:

a) an input device configured for entering patient self-care values $S_M(t_i)$;

b) a memory device configured for storing optimal control parameter values $R(t_i)$ and $R(t_j)$, a prior disease control parameter value $X(t_i)$, optimal self-care values $O_M(t_i)$, and scaling factors $K_M$;

c) a microprocessor, in communication with said input device and said memory device, for calculating a future disease control parameter value $X(t_j)$; and d) a display device configured for displaying said future disease control parameter value $X(t_j)$.

2. The system of claim 1, wherein for each of the at least one disease control parameters, the future disease control parameter value $X(t_j)$ at time $t_j$ is determined from the prior disease control parameter value $X(t_i)$ at time $t_j$ based on the optimal control parameter value $R(t_j)$ at time $t_j$, the difference between said prior disease control parameter value $X(t_i)$ and the optimal control parameter value $R(t_i)$ at time $t_i$, and a set of differentials between patient self-care parameters having the patient self-care values $S_M(t_i)$ at time $t_i$ and optimal self-care parameters having the optimal self-care values $O_M(t_i)$ at time $t_i$, the differentials being multiplied by corresponding scaling factors $K_M$, and the future disease control parameter value $X(t_j)$ is calculated according to the equation:

$$X(t_j) = R(t_j) + (X(t_i) - R(t_i)) + \sum_M K_M(S_M(t_i) - O_M(t_i)).$$

3. The system of claim 1, wherein said microprocessor is capable of determining a general health status of a patient based on simulated disease control parameter values of each of a plurality of disease control parameters.

4. The system of claim 1, wherein said input device comprises means for entering patient self-care values, and said microprocessor is configured for determining at least one of the scaling factors from the patient self-care values entered.

5. The system of claim 1, wherein said input device comprises means for entering patient nutritional values, and said microprocessor is configured for determining at least one of the scaling factors from the patient nutritional values entered.

6. The system of claim 1, wherein said input device comprises means for entering patient risk factor values, and said microprocessor is configured for determining at least one of the scaling factors from the patient risk factor values entered.

7. The system of claim 1 wherein said input device comprises means for entering patient life-style values and said microprocessor is configured for determining at least one of the scaling factors from the patient life-style values entered.

8. The system of claim 1, wherein said input device comprises means for entering one or more patient self-care values, said one or more values selected from the group consisting of Pulmozyme™ usage, pancreatic enzyme usage, bronchodilator usage, antibiotic usage, physical exercise taken, vitamin supplements taken, chest physical therapy, caloric intake, exposure to smokers, and exposure to sneezers; and said microprocessor is configured for determining at least one of the scaling factors from the one or more patient self-care values entered.

9. The system of claim 1, wherein said system comprises a hand-held, freely transportable, virtual pet including a power unit.

10. The system of claim 1, wherein said virtual pet device is capable of simulating a chronic medical condition.

11. The system of claim 1, further including a clock unit, said clock unit synchronized to real time.

12. The system of claim 1, wherein said display device includes a night-light unit.

13. The system of claim 1, wherein the patient self-care values comprise virtual self-care values.

14. The system of claim 1, wherein the patient is a virtual pet capable of simulating a virtual chronic disorder.

15. The system of claim 1, wherein said display device is capable of displaying a plurality of icons thereon.

16. The system of claim 15, wherein said plurality of icons are related to parameters selected from the group consisting of health status, nutrition, and medicine administration.

17. The system of claim 15, wherein said plurality of icons are related to parameters selected from the group consisting of physical therapy, shower, play, school, praise, sleep, and needs attention.

18. The system of claim 1, further comprising a housing, and said input device includes a plurality of buttons arranged on an exterior surface of said housing.

19. The system of claim 1, further comprising an audio unit.

20. The system of claim 19, wherein said audio unit includes a medical regimen factor alarm unit.

21. The system of claim 19, wherein said audio unit includes a Pulmozyme™ alarm.

22. The system of claim 1 wherein the at least one disease control parameter comprises at least one of lung function and body weight.

23. The system of claim 1, wherein the patient self-care parameters comprise at least one of medical regimen adherence and risk factor avoidance.

24. A method for simulating at least one disease control parameter in a simulation system, the method comprising the steps of:
a) providing a simulation system, the simulation system comprising a virtual pet including a microprocessor having a memory, a display connected to the microprocessor, and input device configured for entering in the microprocessor patient self-care values $S_M(t_i)$;
b) storing in the memory optimal control parameter values $R(t_i)$ and $R(t_j)$, a prior disease control parameter value $X(t_i)$, optimal self-care values $O_M(t_i)$, and scaling factors $K_M$;
c) entering in the microprocessor patient self-care values $S_M(t_i)$;
d) calculating in the microprocessor a future disease control parameter value $X(t_j)$, and
e) displaying the future disease control parameter value $X(t_j)$ on the display.

25. The method of claim 24, wherein for each of the at least one disease control parameter, the future disease control parameter value $X(t_j)$ at time $t_j$ is determined from the prior disease control parameter value $X(t_i)$ at time $t_i$ based on the optimal control parameter value $R(t_j)$ at time $t_j$, the difference between the prior disease control parameter value $X(t_i)$ and an optimal control parameter value $R(v)$ at time $t_i$, and a set of differentials between patient self-care parameters having the patient self-care values $S_M(t_i)$ at time $t_i$ and optimal self-care parameters having the optimal self-care values $O_M(t_i)$ at time $t_i$, the differentials being multiplied by corresponding scaling factors $K_M$, and wherein the future disease control parameter value $X(t_j)$ is calculated according to the equation:

$$X(t_j) = R(t_j) + (X(t_i) - R(t_i)) + \sum_M K_M(S_M(t_i) - O_M(t_i)).$$

26. The method of claim 24, further comprising the step of:
f) calculating a general health status score based on the at least one disease control parameter simulated.

27. The method of claim 24, wherein said step c) comprises entering patient self-care values on at least one of the group consisting of: Pulmozyme™ usage, pancreatic enzyme usage, bronchodilator usage, antibiotic usage, physical exercise taken, vitamin supplements taken, chest physical therapy, caloric intake, exposure to smokers, and exposure to sneezers.

28. The method of claim 24, wherein said step d) comprises calculating a future disease control parameter value selected from the group consisting of lung function and body weight.

29. An electronic device for displaying at least one disease control parameter of a fictional patient, comprising:
   a) input device configured for entering self-care values $S_M(t_i)$ of a fictional patient;
   b) a memory for storing optimal control parameter values $R(t_i)$ and $R(t_j)$, a prior disease control parameter value $X(t_i)$, optimal self-care values $O_M(t_i)$, and scaling factors $K_M$;
   c) a microprocessor, in communication with said input device and said memory, for calculating a future disease control parameter value $X(t_j)$; and
   d) a display connected to said microprocessor for displaying the future disease control parameter value $X(t_j)$.

30. The device of claim 29, wherein the future disease control parameter value $X(t_j)$ is calculated according to the equation:

$$X(t_j) = R(t_j) + (X(t_i) - R(t_i)) + \sum_M K_M(S_M(t_i) - O_M(t_i))$$

31. The device of claim 29, further comprising a housing, wherein said memory and said microprocessor are housed within said housing and said display is integral with said housing to provide a hand-held, readily transportable virtual pet device.

32. The device of claim 31, wherein said input device includes a plurality of controls arranged on said housing.

33. A method of motivating a patient to adhere to a medical regimen for a chronic medical condition afflicting the patient, comprising the steps of:
   a) input means for entering patient self-care values;
   b) a memory for storing optimal control parameter values, a prior disease control parameter value, optimal self-care values, and scaling factors;
   c) a microprocessor in communication with said input means and said memory for calculating a future disease control parameter value; and
   d) a display connected to said microprocessor for displaying the future disease control parameter value and wherein said microprocessor is programmed to provide a general health status score of the virtual patient,
   wherein the general health status score is calculated by said microprocessor based on at least two disease control parameter values and
   wherein a future value $X(t_j)$ of each of the at least one disease control parameters at time tj is determined from a prior disease control parameter value $X(t_i)$ at time $t_i$ based on an optimal control parameter value $R(t_j)$ at time $t_j$, the difference between the prior disease control parameter value $X(t_i)$ and an optimal control parameter value $R(t_i)$ at time $t_i$, and a set of differentials between patient self-care parameters having patient self-care values $S_M(t_i)$ at time $t_i$ and optimal self-care parameters having optimal self-care values $O_M(t_i)$ at time $t_i$, the differentials being multiplied by corresponding scaling factors $K_M$, according to the equation:

$$X(t_j) = R(t_j) + (X(t_i) - R(t_i)) + \sum_M K_M(S_M(t_i) - O_M(t_i)).$$

34. The virtual pet of claim 33, wherein the chronic disease afflicting the virtual pet is cystic fibrosis.

* * * * *